(12) United States Patent
Bhaduri et al.

(10) Patent No.: US 8,906,415 B1
(45) Date of Patent: Dec. 9, 2014

(54) CALCIUM PHOSPHATE NANOWHISKER PARTICLES, METHOD OF MAKING AND USING THE SAME

(71) Applicant: The University of Toledo, Toledo, OH (US)

(72) Inventors: Sarit Bhaduri, Holland, OH (US); Darcy E. Wagner, Maumee, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 13/661,215

(22) Filed: Oct. 26, 2012

Related U.S. Application Data

(60) Provisional application No. 61/551,809, filed on Oct. 26, 2011.

(51) Int. Cl.
*A61K 9/14* (2006.01)

(52) U.S. Cl.
USPC .......................................................... 424/489

(58) Field of Classification Search
None
See application file for complete search history.

(56) References Cited

U.S. PATENT DOCUMENTS

| | | | |
|---|---|---|---|
| 2005/0226939 A1* | 10/2005 | Ramalingam et al. | 424/602 |
| 2005/0268819 A1* | 12/2005 | Lin et al. | 106/690 |
| 2011/0046404 A1* | 2/2011 | Sharma et al. | 556/10 |
| 2012/0192481 A1* | 8/2012 | O'Connor | 44/307 |

\* cited by examiner

*Primary Examiner* — Susan Tran
(74) *Attorney, Agent, or Firm* — MacMillan, Sobanski & Todd, LLC

(57) ABSTRACT

Calcium phosphate nanowhisker particles, methods of making and method of using are described.

9 Claims, 22 Drawing Sheets
(8 of 22 Drawing Sheet(s) Filed in Color)

CALCIUM PHOSPHATE NANOWHISKER PARTICLES, METHOD OF MAKING AND USING THE SAME

CROSS-REFERENCE TO RELATED APPLICATIONS

This application claims the benefit of U.S. Provisional Application Ser. No. 61/551,809 filed Oct. 26, 2011, the entire disclosure of which is expressly incorporated herein by reference.

STATEMENT REGARDING FEDERALLY SPONSORED RESEARCH

The invention was made with U.S. Government support under Grant Number CMMI 0753479 awarded by the National Science Foundation. The United States Government has certain rights in the invention.

TECHNICAL FIELD AND INDUSTRIAL APPLICABILITY OF THE INVENTION

The present invention relates to a method of producing homogenous doped calcium phosphate nanowhiskers of various phases, including hydroxyapatite and tricalcium phosphate for use in various applications.

BACKGROUND OF THE INVENTION

Calcium phosphates (CaP) are being investigated for a variety of medical applications ranging from tissue engineering scaffolds to nonviral gene carriers. Examples of prior methods for the formation of calcium phosphate nanoparticles include precipitation techniques, hydrothermal processing, solid state reactions, molten salt synthesis, and microwave-assisted techniques. Chemical synthesis methods are better than traditional solid-state methods in producing nanocrystalline calcium phosphates since solid-state methods often require mechanical mixing of oxides or carbonates after calcinations as well as longer synthesis times. This causes the nanoparticles produced to be of an inferior quality, as observed by their poor sintering behavior, non-homogeneity, and abnormal grain growth.

There is also difficulty in having precise control of the cation stoichiometry. Conversely, chemical processing routes diminish deficiencies associated with diffusion, introduction of impurities, and particle agglomeration. The chemical composition of the particles as well as their morphology and crystallinity are important considerations for medical applications.

In addition, the chemical composition of the material greatly impacts its biocompatibility, bioactivity, and biodegradability. Each calcium phosphate phase has a unique set of attributes due to its crystal structure and availability of calcium and phosphate content. These features greatly impact the manner in which the material will interact with biological systems.

Hydroxyapatite (HA) is the most commonly synthesized calcium phosphate phase, owing to its stability in aqueous solutions and ease of synthesis. HA is also the most similar CaP phase to mammalian bone. While tricalcium phosphate (TCP) is more biodegradable than HA, TCP is more difficult to synthesize, mainly due to the fact that it forms at elevated temperatures and there is a narrow range of parameters at which TCP will be the most stable phase. The majority of synthesis methods currently used to produce TCP nanoparticles are two step processes: precipitation of a precursor, followed by high temperature sintering. It is difficult to transform their morphology into elongated nanoparticles through conventional heating.

SUMMARY OF THE INVENTION

In one aspect, there is provided herein a calcium phosphate nanowhisker particle having a high aspect ratio.

In certain embodiments, the calcium phosphate particles are selected from: hydroxyapatite particles (HA), β-tricalcium phosphate (β-TCP) particles, and a mixture thereof.

In certain embodiments, the particle is characterized by a rod-like dimensional particle shape.

In certain embodiments, the average aspect ratio (length to diameter ratio) of the particle is greater than about 1:1. In certain embodiments, the average aspect ratio of the particle is greater than about 5:1. In certain embodiments, the average aspect ratio of the particle is greater than about 10:1. In certain embodiments, the average aspect ratio of the particle is greater than about 25:1. In certain embodiments, the average aspect ratio of the particle is greater than about 50:1.

In another aspect, the particle can be produced by a process comprising: i) exposing a solution comprised of soluble calcium and soluble phosphate, and optionally one or more additives, to microwave energy; and thereafter, ii) cooling the solution of step i) so that calcium phosphate nanowhiskers are formed.

In certain embodiments, the additive comprises a monovalent ion. In certain embodiments, the additive comprises NaCl.

In a particular aspect, there is provided herein a particle produced by a process comprising: i) providing a mixture of $NaNO_3$, $Ca(NO_3)_2$, $KH_2PO_4$, $HNO_3$, and optionally one or more additives; ii) exposing the mixture of step i) to microwave energy (2.45 GHz, 600 W) for a desired period of time (5 minutes) sufficient to cause exothermic reactions; and iii) cooling the heated mixture of step ii) to produce a high aspect ratio particle.

In another aspect, there is provided herein a therapeutic particle comprising: a) a core of calcium phosphate, the core having a high aspect ratio and a substantially rod shape, and b) a therapeutically active agent comprising at least partially coating the core, whereby an effective amount of the particles can be administered to a subject in need thereof.

In another aspect, there is provided herein a vaccine composition comprising: a) at least one particle described herein, b) a killed, attenuated, or live vaccine, or a decoy virus, or a particle coated with antigenic material, and c) a pharmaceutically acceptable agent or other excipient including nucleic acids, nucleotides, oligonucleotides, peptides to transfect antigen presenting cells (APCs) or non-APCs via the process of cross-presentation.

In another aspect, there is provided herein a method for manufacturing nanowhisker particles, comprising: i) exposing a solution comprised of soluble calcium and soluble phosphate, and optionally one or more additives, to microwave energy; and thereafter, ii) cooling the solution so that calcium phosphate nanowhiskers are formed.

In certain embodiments, the calcium phosphate particles are selected from: hydroxyapatite particles, beta-tricalcium phosphate particles, and mixtures thereof.

In certain embodiments, the soluble calcium salt comprises $Ca(NO_3)_2$ and the soluble phosphate salt comprises $KH_2PO_4$.

In certain embodiments, the reacting step includes mixing an aqueous solution of $Ca(NO_3)_2$ with an aqueous solution of $KH_2PO_4$ at a ratio of about 1:0.38, by weight.

In certain embodiments, the method further comprises including an additive, wherein the additive comprises NaCl; and the additive and soluble calcium salt are present at a ratio of about 3.5:1, by weight.

In another aspect, there is provided herein a calcium phosphate nanowhisker particle for use in gene therapy, gene transfection, drug delivery, magnetic resonance imaging, tumor heat treatment, cell isolation or biosensors.

In another aspect, there is provided herein a calcium phosphate nanowhisker particle for use as a carrier for a biomolecule comprised on one or more of: nucleic acid, nucleotide, oligonucleotide, peptide, protein, antibody and lipid.

In another aspect, there is provided herein a nanoparticle for use in medical therapeutics, comprising: at least one calcium phosphate nanowhisker particle; and an effective amount of at least one therapeutic agent, bound to at least a surface of the calcium phosphate particle.

In another aspect, there is provided herein a bone regenerative composition, comprising a calcium phosphate nanowhisker particle.

In another aspect, there is provided herein an implant comprising: comprising a calcium phosphate nanowhisker particle.

In another aspect, there is provided herein a kit comprising: an implant; and a calcium phosphate nanowhisker particle, formed in a shape for implanting with the implant into a tissue area in need of regeneration.

In another aspect, there is provided herein a method for regenerating connective tissue comprising providing a calcium phosphate nanowhisker particle that is administered to a site in need of tissue regeneration by inserting an implant within the site.

In another aspect, there is provided herein a method for imaging using a fluorescent calcium phosphate nanowhisker probe doped with a lanthanide series rare earth such as La, Ce, Pr, Nd, Pm, Sm, Eu, Gd, Tb, Dy, Ho, Er, Tm, Yb, Lu, and the like.

In certain embodiments, the calcium phosphate nanowhisker is doped with Eu and Tb.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the Patent Office upon request and payment of the necessary fee.

DETAILED DESCRIPTION

Figure 1:
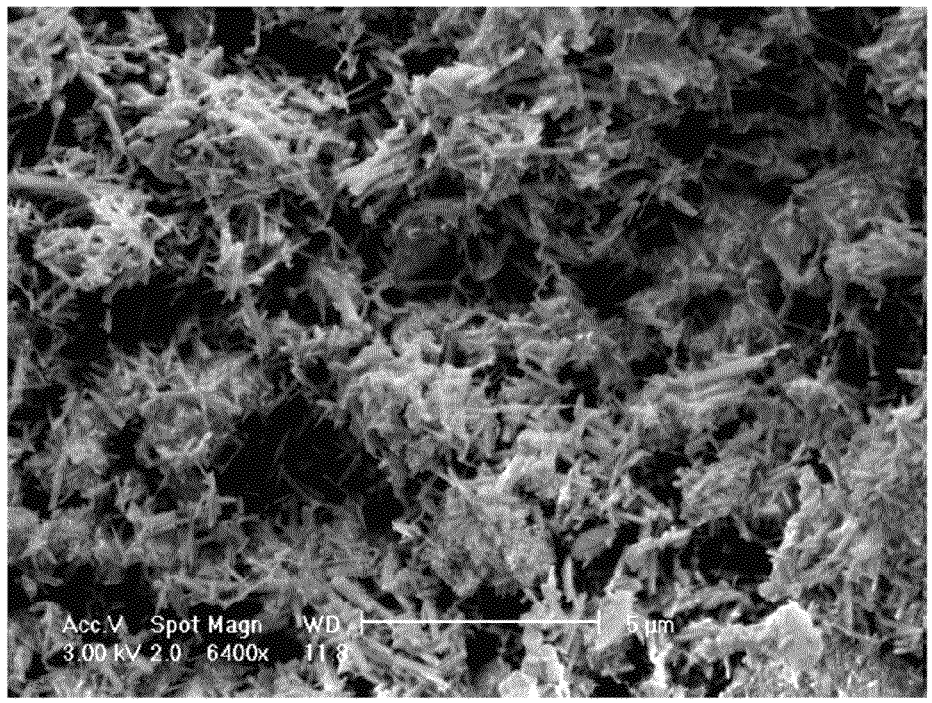
FIG. 1—SEM Micrograph of HA Nanowhiskers showing controlled morphology.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Described herein are methods of producing structures and devices by use of techniques of nanotechnology. The invention also relates to methods of producing nanostructures having nanometer dimensions where its length is greater than its width or its diameter. For the purposes of this application, such an element will be termed a "nanowhisker."

The nanowhisker particles described herein are useful as an active agent delivery system where the nanowhisker particle can be conjugated to an active agent ("conjugates"). In one example, the active agent can be adsorbed onto the nanowhisker particles. The high aspect ratio of the nanowhisker particle described herein provides a high surface area which allows for the adsorption of large quantities of an active agent that can then be released in a controlled fashion into a patient. The high active agent loading capacity of the nanowhisker particles allows for only small (yet therapeutically effective) quantities of the nanowhisker particles to be needed in therapeutic treatments.

Also described herein is a method to treat or prevent a disease condition in a patient which can include administering to a patient in need thereof an active agent delivery system comprised of the nanowhisker-particle-active-agent-conjugate.

The active agent delivery systems can be used for localized, less toxic active agent therapy delivery, for example the delivery of chemotherapeutic agents. The nanowhisker particles are stable, provide immediate and sustained release, are biocompatible, biodegradable, and have non-toxic and non-acidic degradation products.

By targeting the active agent delivery, enhanced active agent efficacy can result from localized active agent application. It is to be understood that the calcium phosphate in the nanowhisker particle is biocompatible and will not cause inflammation and soft-tissue calcification, making it especially suitable for treatment of soft tissue.

Depending upon the active agent present in the conjugate, the nanowhisker particle active agent conjugate can be used to treat a wide variety of disease conditions or disorders by the administration of a therapeutically effective amount of the active agent in the form of a nanowhisker particle active agent conjugate. An "effective amount" or a "therapeutically effective amount" of an active agent means a sufficient amount of the active agent to provide the desired effect. The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation.

The nanowhisker particle active agent conjugates ("conjugates") can be prepared by adsorbing an active agent to the nanowhisker particle. To form the conjugates, the active agent can be mixed with the nanowhisker particles and incubated, optionally in the presence of a pharmaceutically acceptable vehicle.

The nanowhisker particles can be conjugated with any suitable active agent and/or biomolecules, owing at least in part, to the nanowhisker particle structure/shape. It is to be understood that diverse types of active agents can be used. Non-limiting examples include: adrenergic agents, analgesics, angiotensin-converting enzyme (ACE) inhibitors, anti-anxiety agents, anti-arrhythmic agents, anti-bacterial agents, antibiotics, anti-cancer agents, anti-depressants, anti-diabetics, anti-epileptics, anti-fungal anti-helminthics, anti-hyperlipidemics, anti-hypertensive agents, anti-infectives, anti-malarials, anti-microbials, anti-migraine agents, anti-muscarinic agents, anti-neoplastic agents, anti-protozoal agents, anti-psychotic agents, anti-viral agents, beta-blockers, calcium channel blockers, chemotherapeutic agents, cholinesterase inhibitors, Cox-2 inhibitors, hypnotics, hypotensive agents, immunosuppresants, lipotropics, opioid analgesics, peripheral vasodilators/vasoconstrictors, sedatives, serotonin receptor agonists, targeting ligands, and the like.

Non-limiting examples of anti-cancer agents include: aminoglutethimide, busulfan, carmustine, chlorambucil, cisplatin, cyclophosphamide, cytarabine, dacarbazine, daunorubicin, diethylstilbestrol, doxorubicin, etoposide, fluorouracil, fluoxymesterone, flutamide, gemcitabine, goseraline acetate, hydroxyprogesterone, hydroxyurea, leuprolide, lomustine, mechlorethamine, medroxyprogesterone acetate, megestrol acetate, melphalan, mercaptopurine, methotrexate, paclitaxel, prednisone, procarbazine, tamoxifan, testosterone propionate, thioguanine, vinblastine, vincristine, vindesine, vinorelbine, pharmaceutically acceptable salts thereof, and combinations thereof.

Also, in certain embodiments, the nanowhisker-particle-active-agent-conjugate can further include other agents. It is to be understood that various other agents can be adsorbed on the nanowhisker particles; for example, to improve imaging, to improve cellular uptake, to modify active agent release, for combination therapy, and the like. In another example, the nanowhisker particles can be with a dispersing agent.

The nanowhisker-particle-active-agent-conjugate can be formulated in any suitable manner, non-limiting examples of which include: an injectable formulation for delivery though any suitable means, including, but not limited to, a needle, a syringe, a cannula, or other suitable means.

In use, the nanowhisker-particle-active-agent-conjugate can be delivered in any suitable manner, non-limiting examples of which include: subcutaneous injection, intradermal injection, intratumoral injection, peritumoral injection, intramuscular injection, intravenous injection, and the like.

Also described herein is a method of making the nanowhisker particles which includes a microwave-assisted process that results in more uniform volumetric heating than conventional heating methods. This more uniform volumetric heating provides a desirable formation of nanowhisker particles having a high length:diameter aspect ratio, and also reduces the energy consumption necessary for the reaction.

In particular, described herein are the effects of concentration, solution additives, and the effect of cooling rate on the final nanoparticle shape and chemical phase.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain preferred embodiments of the invention and should not be interpreted to limit the scope of the invention as defined in the claims, unless so specified.

The value of the present invention can thus be seen by reference to the Examples herein.

Example 1

Nanoparticle Synthesis

All chemicals were purchased from Fisher Scientific (Fisher Chemicals, Fisher Scientific, Fair Lawn, N.J.). Moving sequentially from left to right, the given amounts of each chemical listed in Table 1 through Table 3 were dissolved in 10 mL of de-ionized water in a 30 mL Pyrex beaker under constant stirring then placed in a household microwave oven (Emerson MW87817SB, 2.45 GHz, 600 W) in a fume hood and heated at full power for a desired period of time, for example 5 minutes. One additional sample was prepared to study the effect of cooling rate on the resultant nanowhisker formation.

TABLE 1

Sample Preparation for HA, TCP and Biphasic Nanowhiskers

| Sample | $NaNO_3$ (g) | $Ca(NO_3)_2 4H_2O$ (g) | $KH_2PO_4$ (g) | 15.69M $HNO_3$ (mL) | Urea (g) | Cooling conditions |
|---|---|---|---|---|---|---|
| HA-1 | 5.00 | 1.00 | 0.345 | 0.10 | 1.75 | 10-15 min air |
| TCP-1 | 5.00 | 1.00 | 0.38+ | 0.10 | — | 10-15 min air |
| Biphasic-1 | 5.00 | 1.00 | 0.345 | 0.10 | 0.75 | 10-15 min air |

Table 2 shows the TCP Precursors prepared with different urea concentrations.

TABLE 2

TCP Precursors prepared with Different Urea Concentrations

| Sample | $NaNO_3$ (g) | $Ca(NO_3)_2 4H_2O$ (g) | $KH_2PO_4$ (g) | Urea (g) | Cooling conditions |
|---|---|---|---|---|---|
| TCP-025 | 5.00 | 1.00 | 0.384 | 0.25 | 10-15 min air |
| TCP-050 | 5.00 | 1.00 | 0.384 | 0.50 | 10-15 min air |
| TCP-100 | 5.00 | 1.00 | 0.345 | 1.0 | 10-15 min air |
| TCP-125 | 5.00 | 1.00 | 0.345 | 1.25 | 10-15 min air |
| TCP-150 | 5.00 | 1.00 | 0.345 | 1.50 | 10-15 min air |
| TCP-200 | 5.00 | 1.00 | 0.345 | 2.0 | 10-15 min air |

Table 3 shows the sample preparations for calcium-phosphate nanowhiskers (CaPnw) with different additives.

TABLE 3

Sample Preparations for CaPnw with Additives

| Sample | $NaNO_3$ (g) | Additive (g) | $Ca(NO_3)_2 4H_2O$ (g) | $KH_2PO_4$ (g) | 15.69M $HNO_3$ mL) | Urea (g) |
|---|---|---|---|---|---|---|
| TCP-EDTA | 5.00 | 1.07 | — | — | — | — |
| TCP-Mg | 4.42 | 0.860 | 1.00 | 0.384 | 0.10 | — |
| TCP-NaCl | 5.00 | 3.43 | 1.00 | 0.384 | 0.10 | |

TCP-1, listed in Table 1, was placed inside of an alumina insulation box during microwave combustion and then cooled. The sample was surrounded by alumina fibers to insulate the beaker during cooling. After the samples had cooled and solidified, the resultant substance was removed from the beaker, placed in 500 mL of de-ionized water and magnetically stirred at 400 RPMs for one hour. The solution was then poured through a Buechner funnel lined with filter paper (Whatman Grade 4, 1004-055) and washed with approximately 2 L of de-ionized water to remove all residual ions. The filtrand was then placed in an oven for 2 hours at 80° C. and allowed to dry. The resultant powder was crushed in a granite mortar and pestle and stored for analysis.

Sample Characterization

Samples were analyzed by X-ray diffraction (XRD) (Ultima III, Rigaku, Woodlands, Tex.), scanning electron microscopy (SEM) (S-4800, Hitachi, Tokyo, Japan), and transmission electron microscopy (TEM) (HD-2300, Hitachi, Tokyo, Japan). The XRD spectra of the powders were obtained over a 2θ range of 20° to 60° with a step size of 0.02° and a scan rate of 0.5θ/s. The data was collected using a Cu K-α monochromator in the focused beam mode. SEM and TEM samples were prepared by ultrasonically dispersing small amounts of the powders in 70% ethanol for 2 minutes. 5 μL of the solution was placed on carbon conducting tape on SEM sample mounts or holey copper grids for SEM/TEM analysis and allowed to air dry. SEM samples were sputter coated with gold prior to imaging. SEM images were obtained at accelerating voltages of 3 kV, 7 kV, and 15 kV. TEM images were obtained at an accelerating voltage of 200 kV.

Results for Example 1

Characterization of Standard Synthesis Nanoparticles

SEM and TEM were used to characterize the nanoparticles' morphology. FIG. 1 shows the HA nanowhiskers and confirms that the HA formulation resulted in the majority of nanoparticles tending towards high aspect ratios. As used herein, the term aspect ratio is defined as length/diameter.

Figure 2:
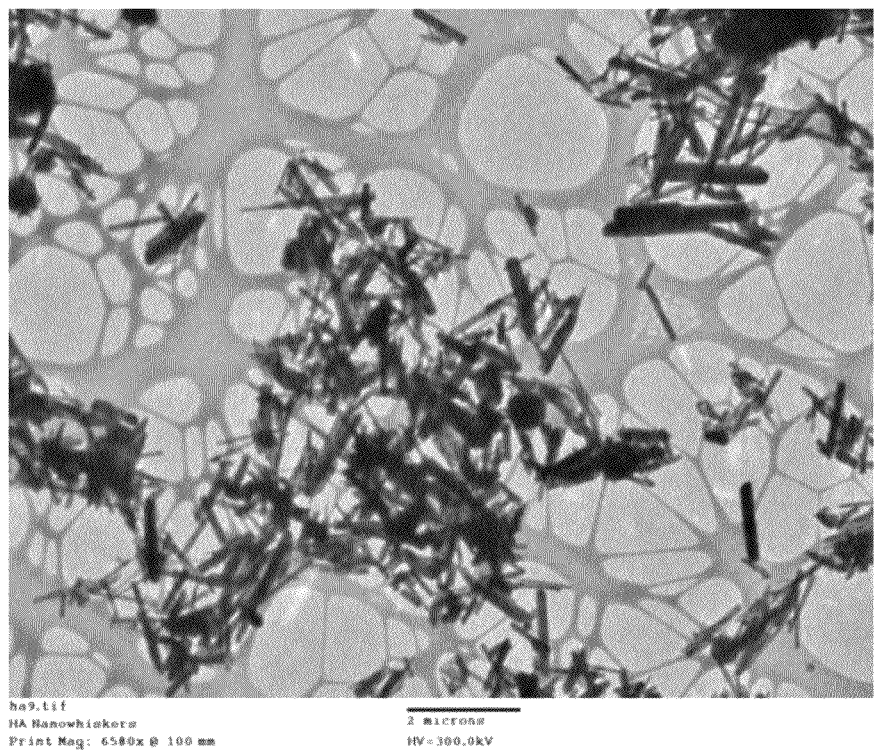
FIG. 2—TEM Micrograph of HA Nanowhiskers showing uniform shape.

The TEM micrograph in FIG. 2 confirms that most particles are less than 2 nm in length and range from 50 nm to 200 nm in length.

Figure 3:
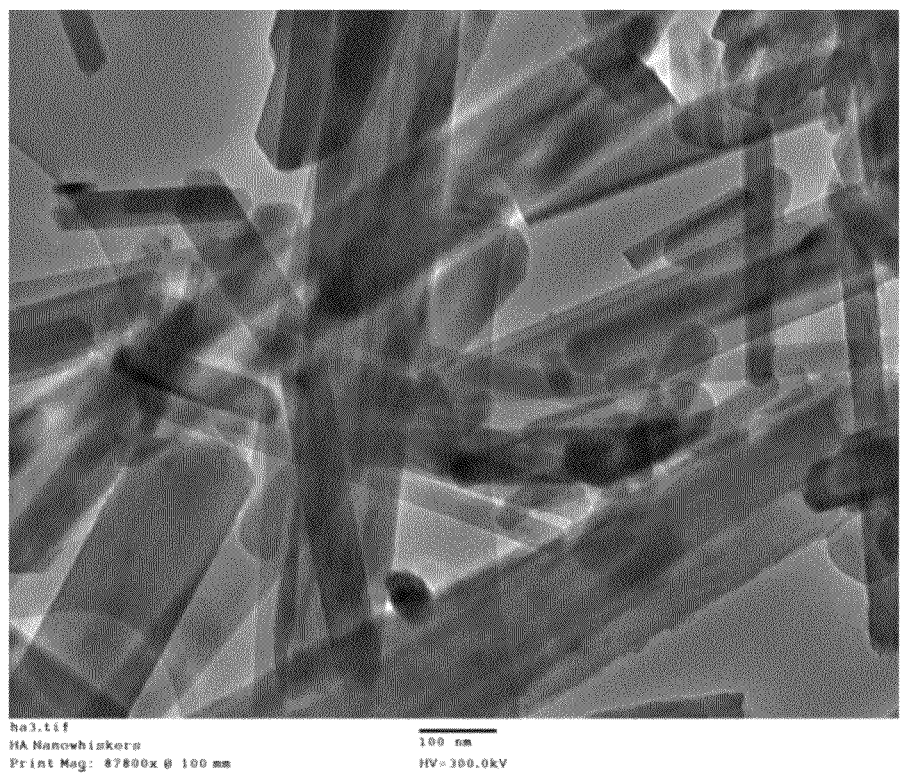
FIG. 3—TEM micrograph showing single nanoparticles.

FIG. 3 confirms that the particles are non agglomerated, single particles.

Figure 4:
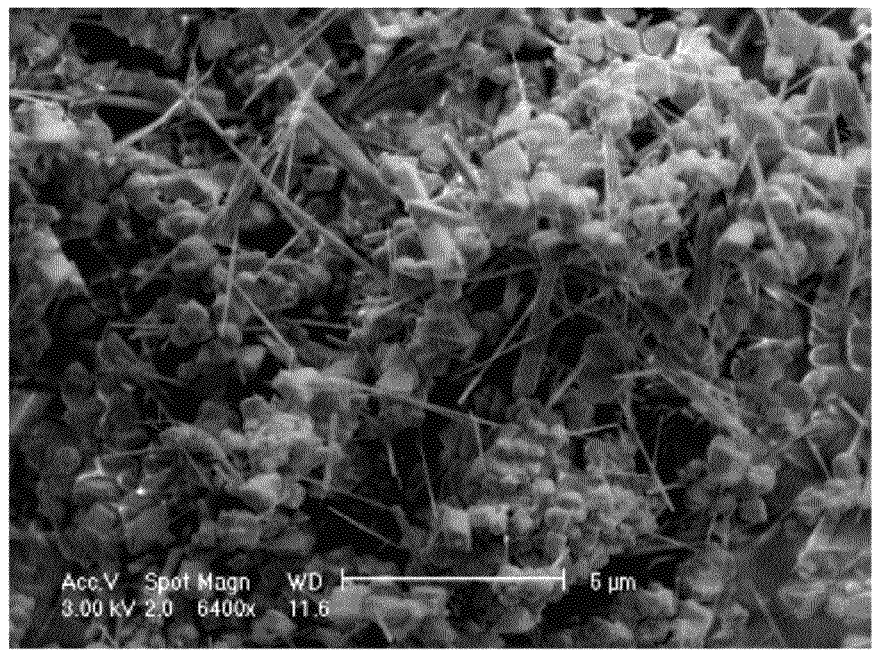
FIG. 4—SEM micrograph of TCP-1 showing nonhomogenous shape synthesis with the majority of nanoparticles having an aspect ratio nearing one. Some high aspect ratio nanowhiskers were present in the TCP-1 formulation.

While TCP-1 lacked morphological homogeneity, as shown in FIG. 4, some high aspect ratio (AR) nanoparticles were present—ranging from around 5-20 AR. As used herein, the term "high aspect ratio" is defined as an average AR of about 5:1 or greater, including but not limited to an average AR greater than about 10:1, an average AR greater than about 25:1, and an average AR greater than about 50:1. Additionally, an average AR greater than about 1:1 may be considered a high aspect ratio.

Figure 5:
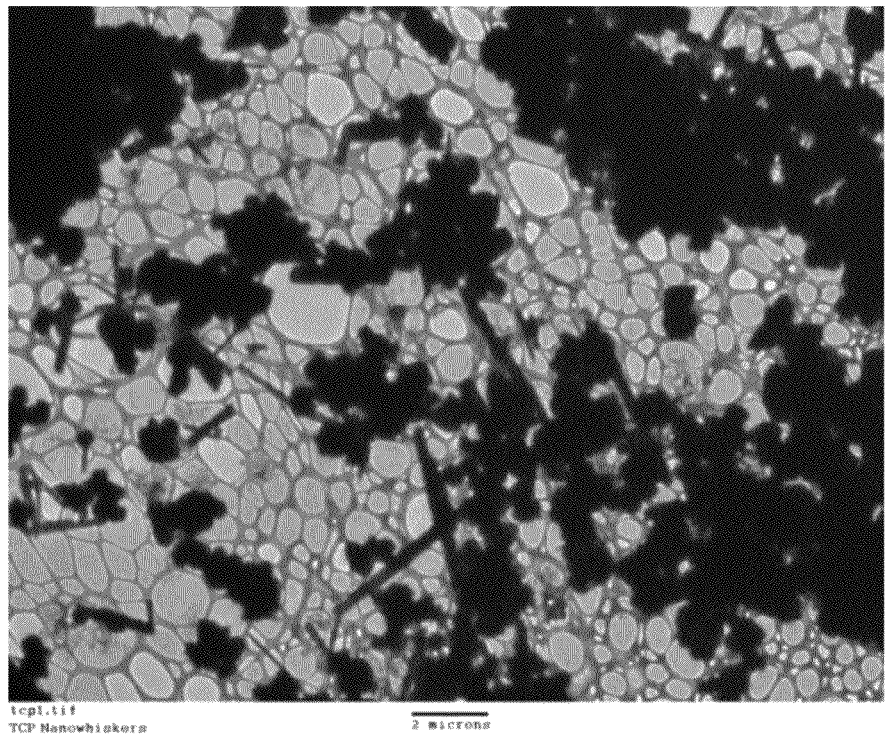
FIG. 5—TEM micrograph of TCP-1 confirming the SEM observations of nonhomogeneous nanoparticle synthesis.
Figure 6:
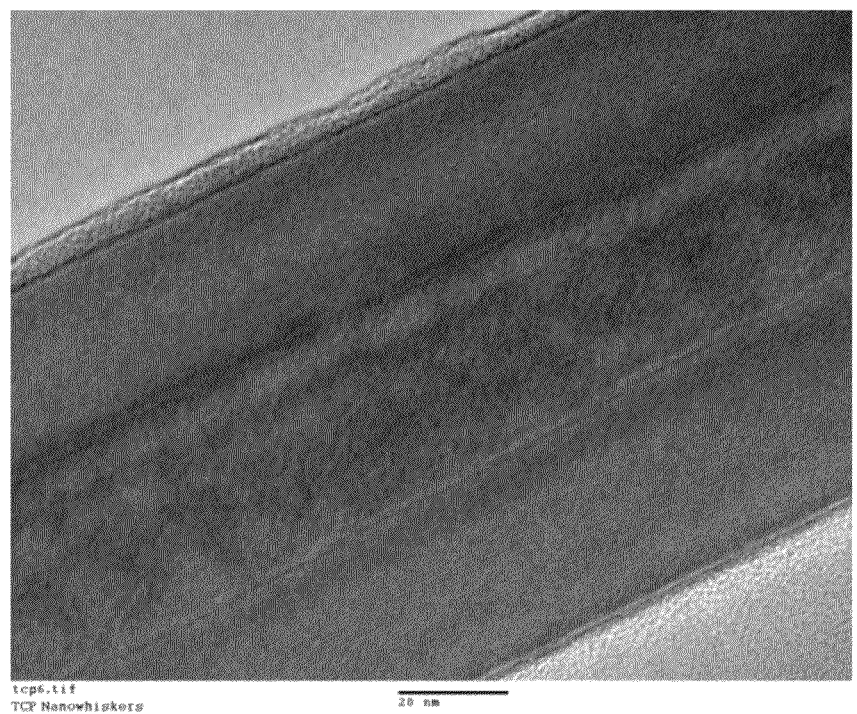
FIG. 6—TEM Micrograph of TCP-1 showing the synthesis of a potential nanotube.

FIG. 5 confirms that the majority of particles from TCP-1 had aspect ratios around 1 with very few high AR particles forming. One interesting feature found with the TCP-1 formulation was that some of these nanowhiskers are hollow. An example is shown in the TEM micrograph in FIG. 6, showing a hollow calcium phosphate nanoparticle with a high aspect ratio. Further, in several embodiments, a number of formed nanowhiskers are hollow. This provides additional advantages since inorganic, hollow structures have unique properties that are advantageous in medical applications.

Figure 7:
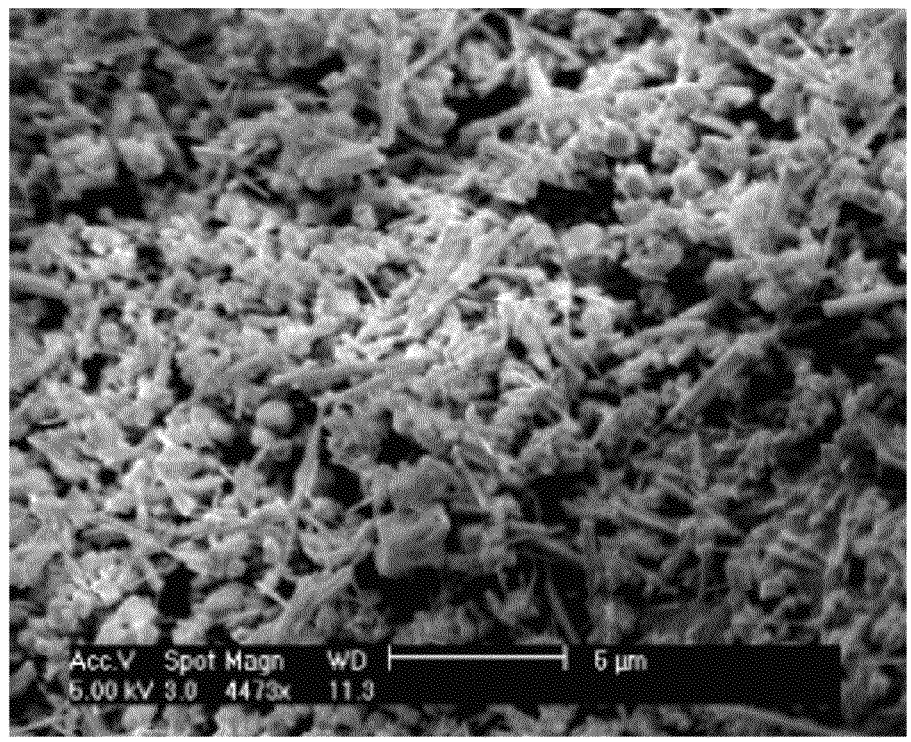
FIG. 7—SEM micrograph of biphasic formulation showing a mixture of both high and aspect ratio one particles.

Also, in certain embodiments, as a material, calcium phosphate may be more advantageous than the other structures such as carbon, silica, and iron oxide nanotubes owing to its high biocompatibility and chemical similarity to mammalian bone. The biphasic composition had higher aspect ratio nanoparticles than the TCP-1 formulation, as seen in FIG. 7.

Figure 8:
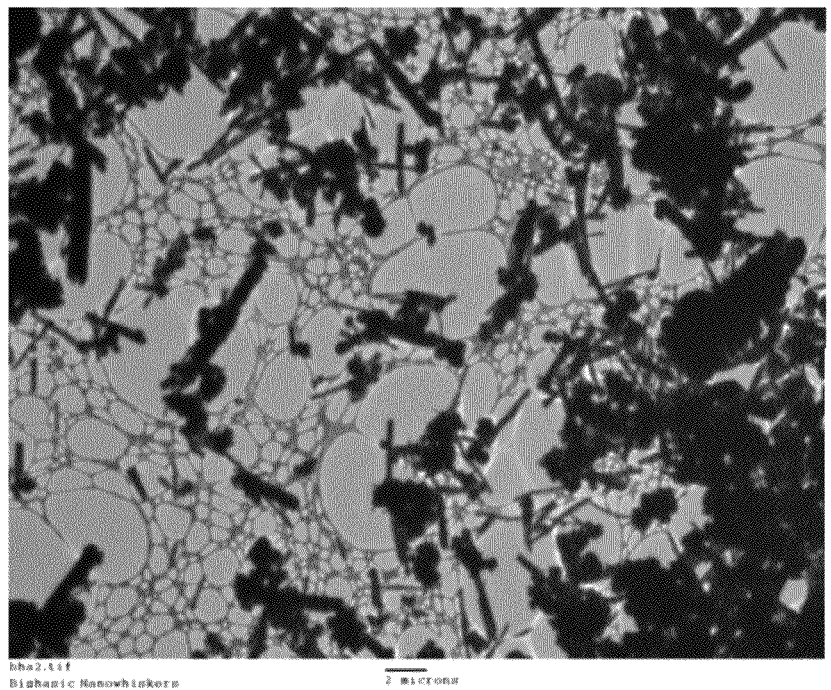
FIG. 8—TEM micrograph of biphasic nanoparticles showing both high aspect ratio nanoparticles and nanoparticles with aspect ratio of one.
Figure 9:
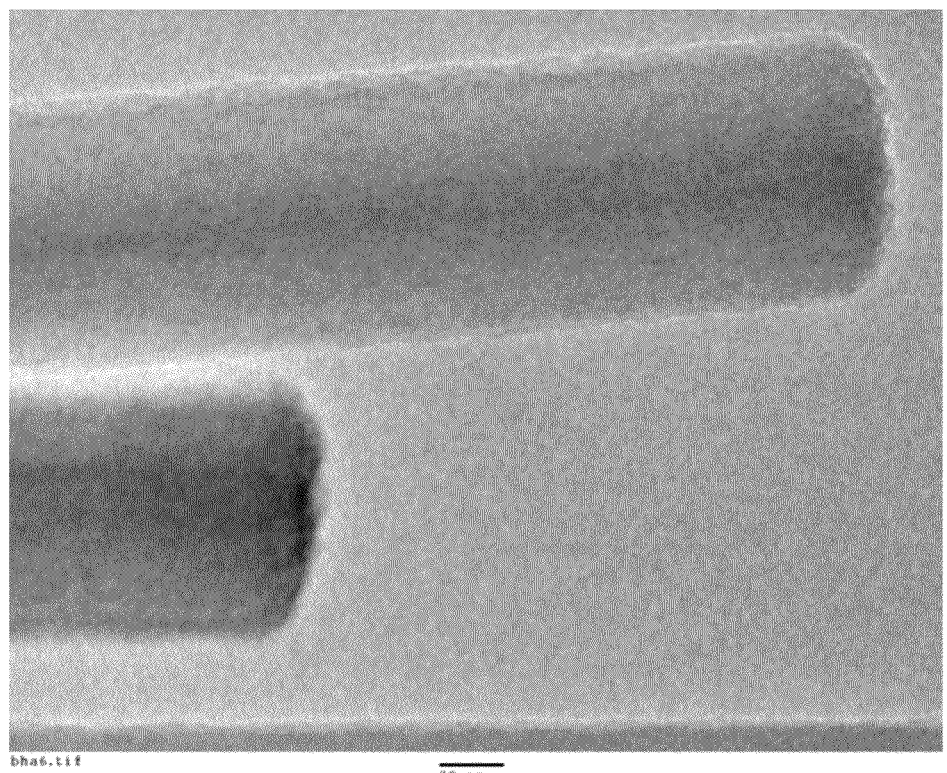
FIG. 9—TEM micrograph showing biphasic nanoparticles with high aspect ratio.

The TEM micrographs of FIG. 8 and FIG. 9 show that there is a combination of nanoparticles with an aspect ratio of 1 as well as high AR particles. In these embodiments, the biphasic morphology appears to be a blend of the two other synthesis methods.

Figure 10:
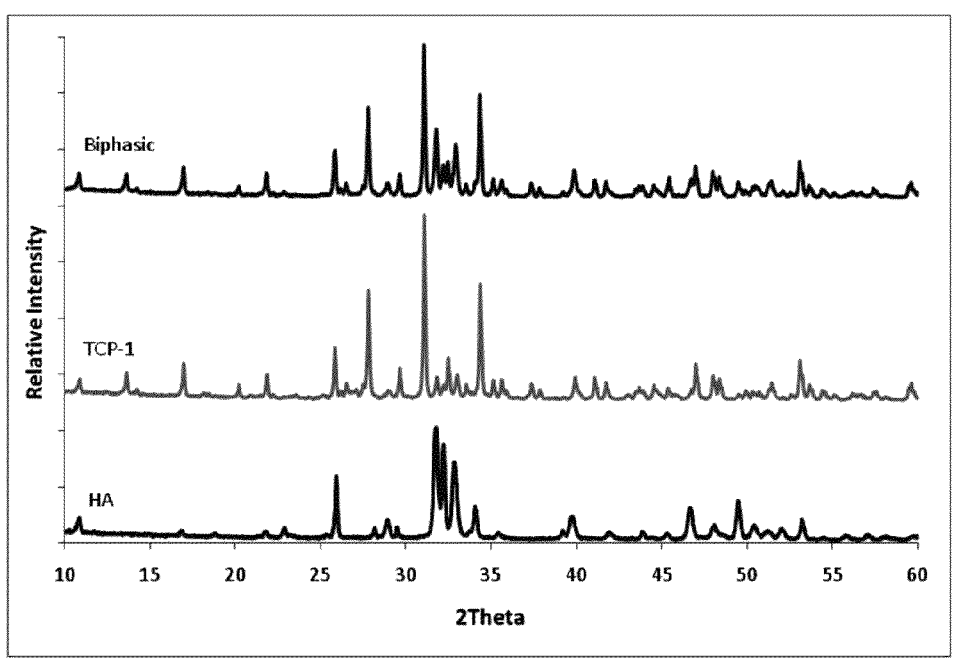
FIG. 10—XRD Patterns of the as-synthesized nanoparticles.
Figure 11:
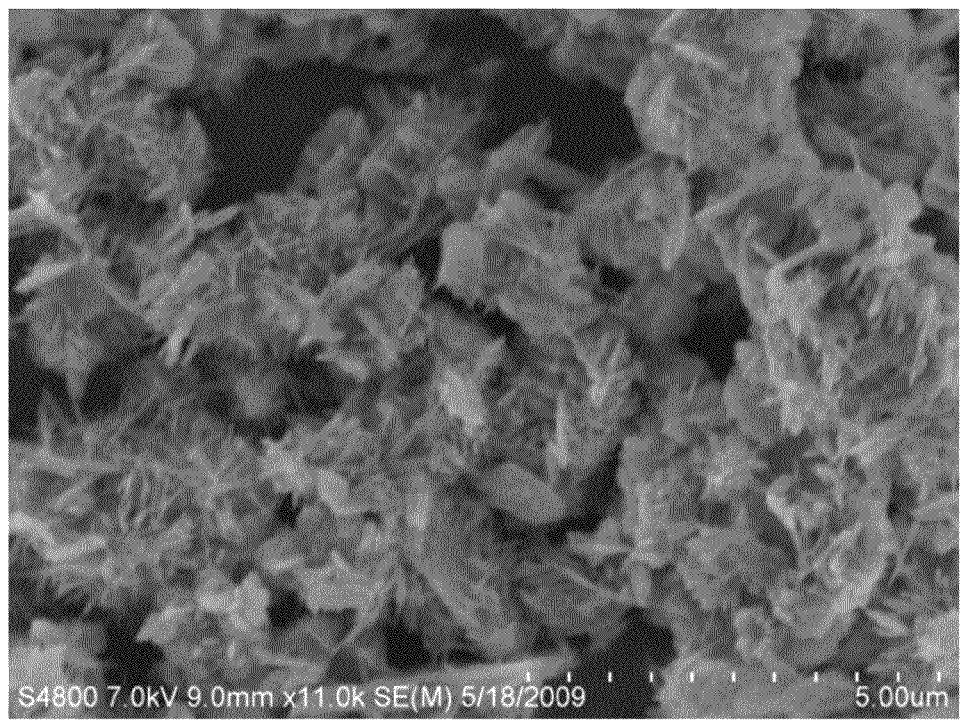
FIG. 11—TCP-025 showing increasing nanowhisker formation.
Figure 12:
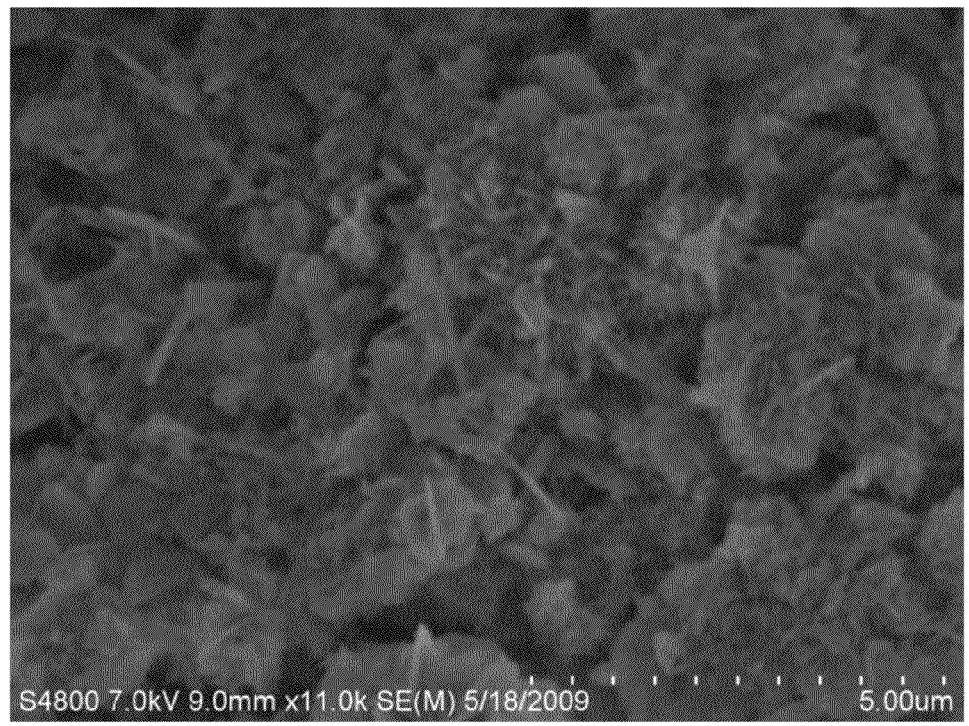
FIG. 12—TCP-050 showing further increase in the number of high aspect ratio nanoparticles.
Figure 13:
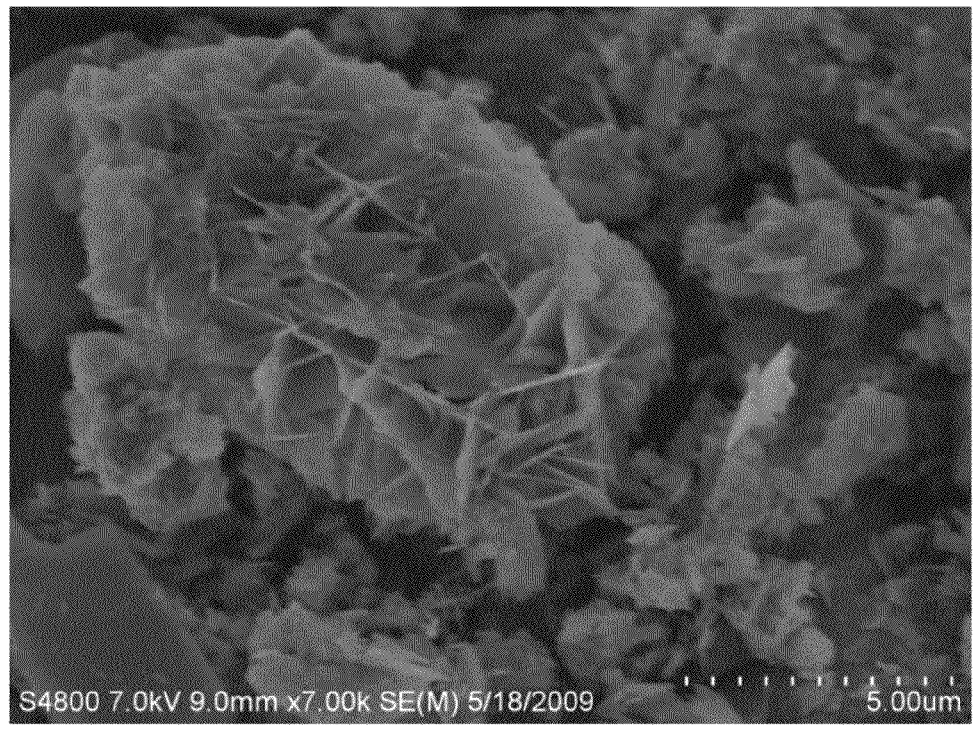
FIG. 13—TCP-10 showing nanoparticles synthesized with low crystallinity and low aspect ratios.

FIG. 10 shows the XRD traces of the as-synthesized compositions. The three peaks, beginning at 31.7, are characteristic of synthetic HA and can be seen for both the HA and biphasic formulations. In the case of TCP-1, the phase was confirmed as β-TCP. However, by examining the SEM and TEM micrographs, it can be seen that the majority of the nanoparticles do not have a high AR. The XRD did not show traces for individual particles and identifies phases by bulk powder diffraction. While not wishing to be bound by theory, the inventors herein now believe that it is possible that none of the nanowhiskers synthesized using this formulation are actually of the β-TCP variant because they are present at such low concentrations.

The biphasic formulation was capable of producing both TCP and HA particles with a high AR, but nanoparticles with an aspect ratio of one were still present.

Effect of Urea Concentration

The amount of urea that is present in the solution can be related to the percentage of powders that are converted into whiskers. An initial calcium phosphate ratio for TCP was used as the base formulation, but the urea content was changed from 0 to 0.25, 0.5, 1.0, 1.25, 1.5, and 2.0. Increasing the urea content improves the combustion ratio; and, as a result, the reaction temperature and the amount of gas produced.

The reaction temperature can help drive the phase of the material towards TCP, which is normally synthesized at much higher temperatures than HA. Increases in gas production leads to an increase in the amount of fine particulates. Therefore, the urea-to-nitrate ratio was altered in order to improve the morphology of the resulting nanoparticles.

Figure 14:
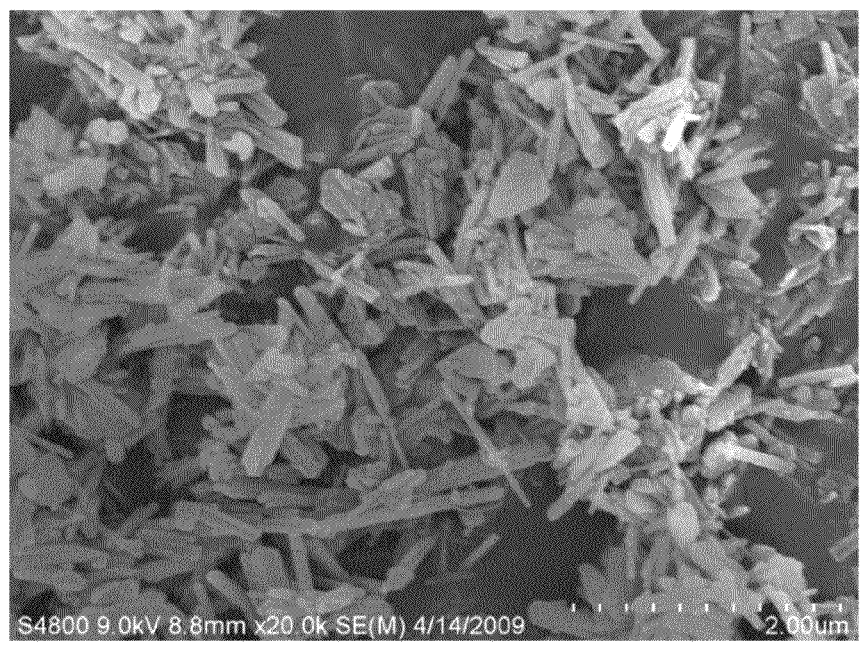
FIG. 14—SEM micrograph of TCP-20 showing shape uniformity.

As can be seen in FIGS. 11-14, the initial small increase of urea content increased the amount of nanoparticles synthesized that had a high aspect ratio. However, as can specifically be seen in FIG. 13, at 1.0 g of the addition of urea, the nanowhisker morphology seemed to disappear, and additionally, the particles produced appeared to lack crystallinity. Further addition of urea was successful in producing more nanoparticles with high aspect ratios, as shown in FIG. 14.

Figure 15:
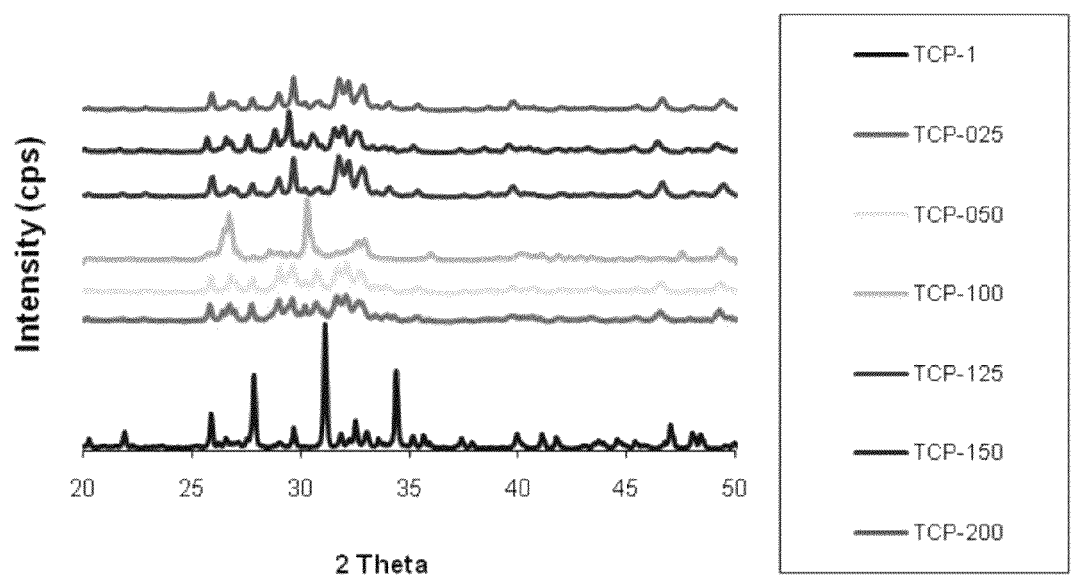
FIG. 15—XRD Trace showing the effects of increasing urea content for the TCP-1 formulation.

As can be seen in the XRD trace shown in FIG. 15, as the amount of urea increases, the resultant nanoparticles actually begin to change phase. Despite an initial Ca/P ratio of 1.5 and therefore TCP, the material tended towards the HA phase. While the increase in urea may optimize the combustion ratio, when urea decomposes there will be a concomitant change in pH. TCP is most stable at a pH between 4-5, thus an increase in pH will also drive the resultant calcium phosphate precipitated in the molten salt bath to be HA. Therefore, solution pH during nanoparticle formation is a dominant factor over the initial chemical ratios in predicting final chemical phases.

Effect of EDTA

Figure 16:
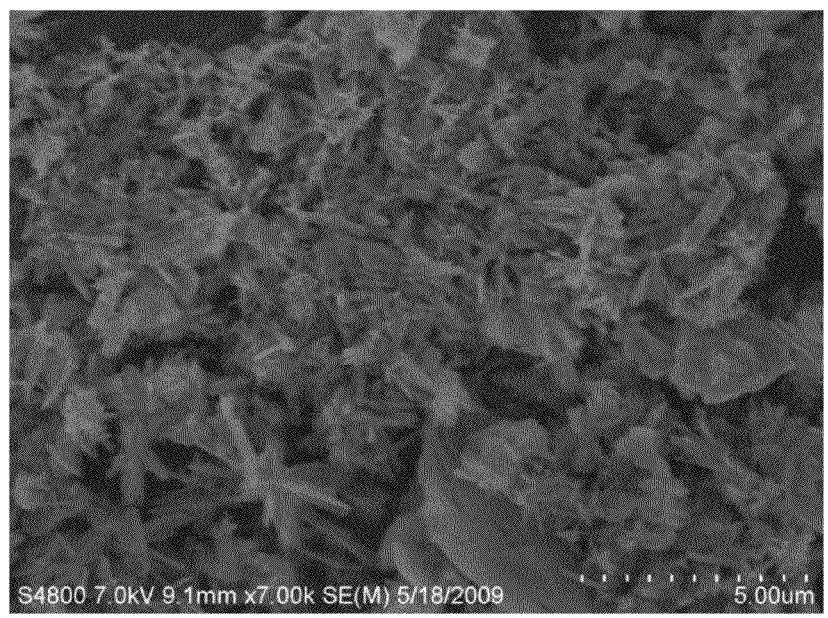
FIG. 16—SEM Micrograph of TCP with the addition of EDTA.

EDTA produces flower-like morphologies of hydroxyapatite during simple microwave irradiation. EDTA was added to the hydroxyapatite formulation after the sodium nitrate was dissolved. The SEM Micrograph in FIG. 16 confirms that a growth mechanism occurs in the microwave combustion synthesis process. As the urea breaks down in the solution there is an increase in solution pH. Therefore, the flower-like morphologies produced here are stable complexes generated through the initial complexation of calcium to the EDTA molecule with further crystal growth from these new nucleation sites during cooling.

Effect of Magnesium on Crystal Growth

While the presence of ample nitrate is needed for combustion and an optimal ratio between nitrate and urea exists, the choice of a nitrate source is also important as it may introduce other ions that may impact crystal growth kinetics.

Figure 17:
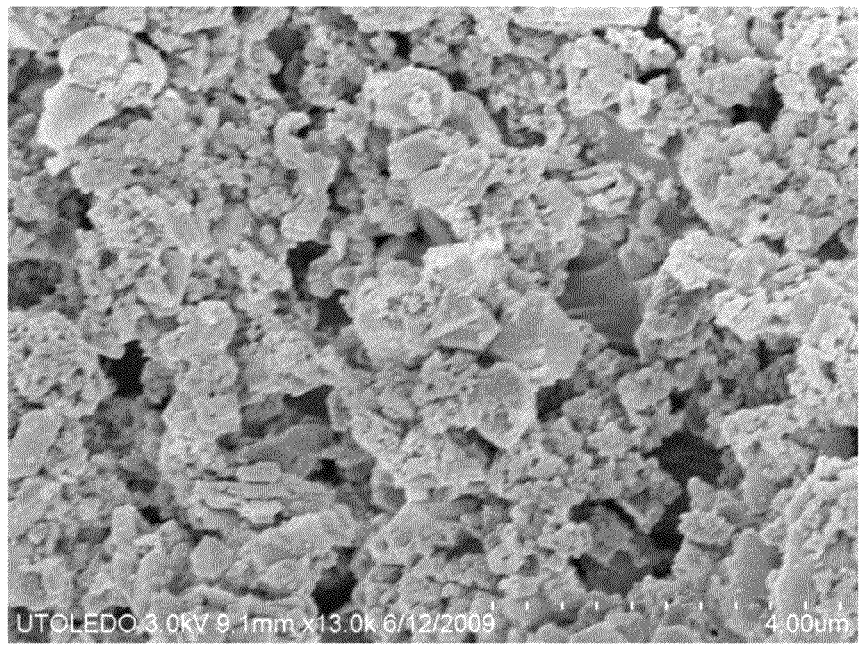
FIG. 17—HA with magnesium nitrate substituted for sodium nitrate with nitrate amount held constant.

As can be seen in FIG. 17, changing the initial salt from sodium nitrate to magnesium nitrate in the HA formulation while keeping nitrate content constant, drastically changes the resultant nanoparticle morphology. Despite the nitrate content being held constant, and therefore combustion properties also remaining similar, the resultant crystal growth is affected. The particles are significantly smaller and have an aspect ratio of approximately one.

Calcium and magnesium are both divalent cations and therefore during solution cooling, which is when crystal growth occurs, magnesium may also preferentially bind to the phosphate ions and precipitate out. In effect, this prevents the calcium phosphates from extensive crystal growth.

Figure 18:
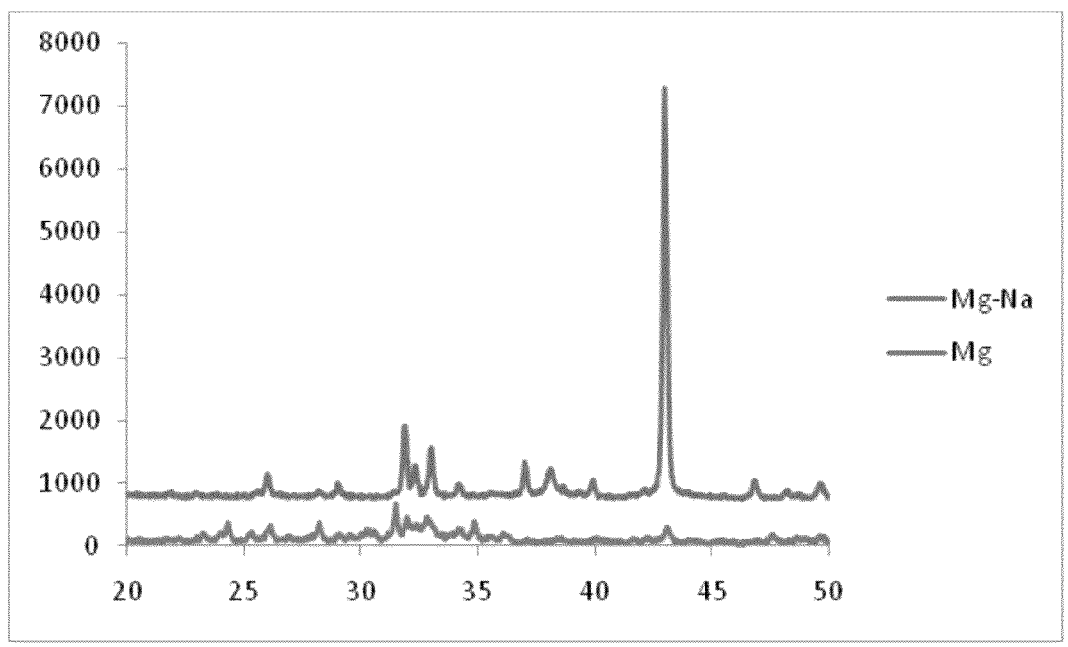
FIG. 18—XRD Traces showing the influence of magnesium on the resultant nanoparticle phase. Mg represents complete substitution of magnesium nitrate for sodium nitrate while Mg—Na represents 50% of the nitrate coming from $Mg(NO_3)_2$ and 50% from $NaNO_3$.

The XRD trace shown in FIG. 18 confirms that the resultant material is not a pure calcium phosphate phase but a composition of calcium phosphate and magnesium phosphate phases. The characteristic HA peaks are present confirming that the HA phase was still the CaP phase formed.

Effect of the Addition of Sodium Chloride

Figure 19:
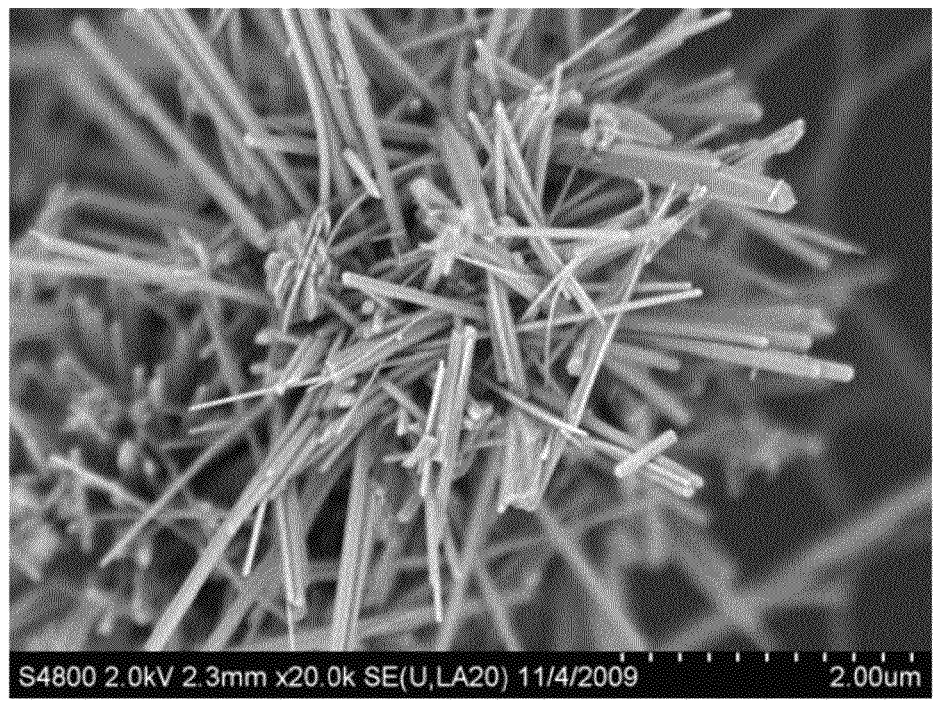
FIG. 19—SEM Micrograph of TCP formulation with the addition of NaCl (TCN) showing increasing number of nanowhiskers.
Figure 20:
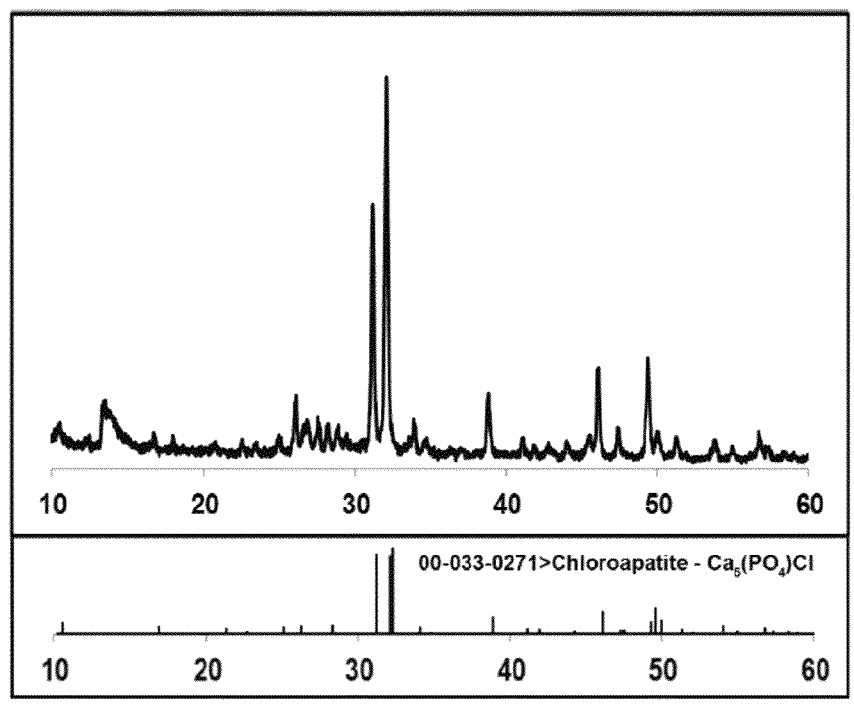
FIG. 20—X-ray diffraction patterns for the nanowhiskers in FIG. 19; chloroapatite peaks denoted.

Nucleating agents can be used to increase the number of nucleation sites present during crystal growth. The nanowhiskers form by a sequential nucleation-solidification-nucleation method along the c-axis. Adding sodium, a monovalent ion, assists in providing additional nucleation sites and/or changing the solubility kinetics during cooling to promote calcium phosphate precipitation to drive the growth along the c-axis. As can be seen in FIG. 19, the addition of NaCl increases the number of nanowhiskers formed and improved the homogeneity of the resultant shape. The nanoparticles show an increase in both morphology and uniformity of the nanowhiskers synthesized. FIG. 20 shows the XRD data for the TCP-1 formulation with the addition of NaCl.

The calcium phosphate nanowhisker particles, produced using the microwave assisted method described herein provides a way to produce a shape homogenous composition of chloroapatite nanowhiskers through the addition of sodium chloride.

Effect of Cooling Rate on the Aspect Ratio of Formed Nanoparticles

Alumina is transparent to microwave irradiation, therefore the reaction kinetics during combustion will not differ if alumina insulation is used. However, an alumina construct can provide insulation during cooling and thus slow the cooling rate.

Figure 21:
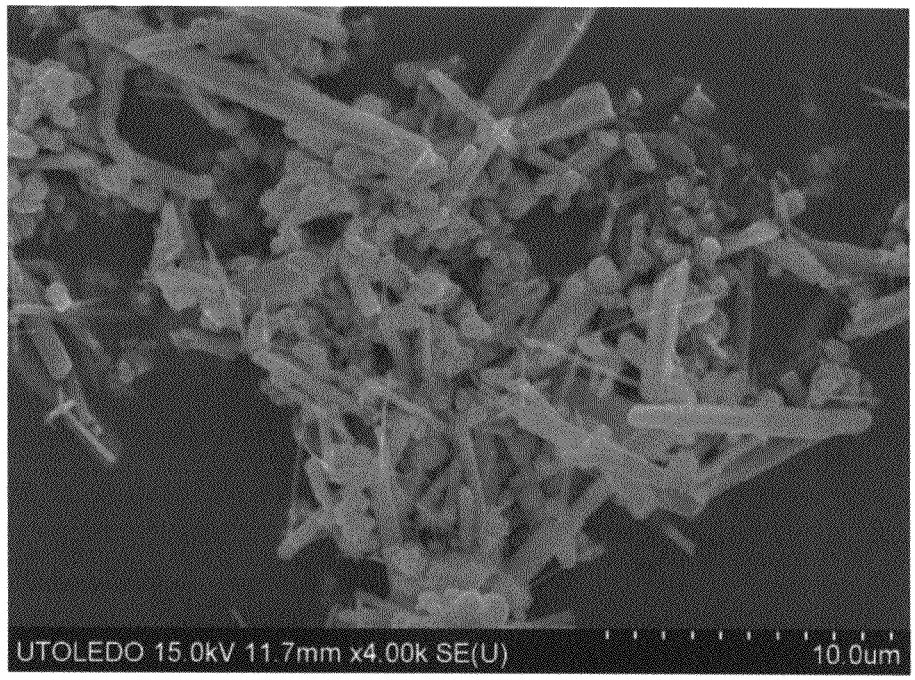
FIG. 21—SEM Micrograph of TCP-SC Nanowhiskers.
Figure 22:
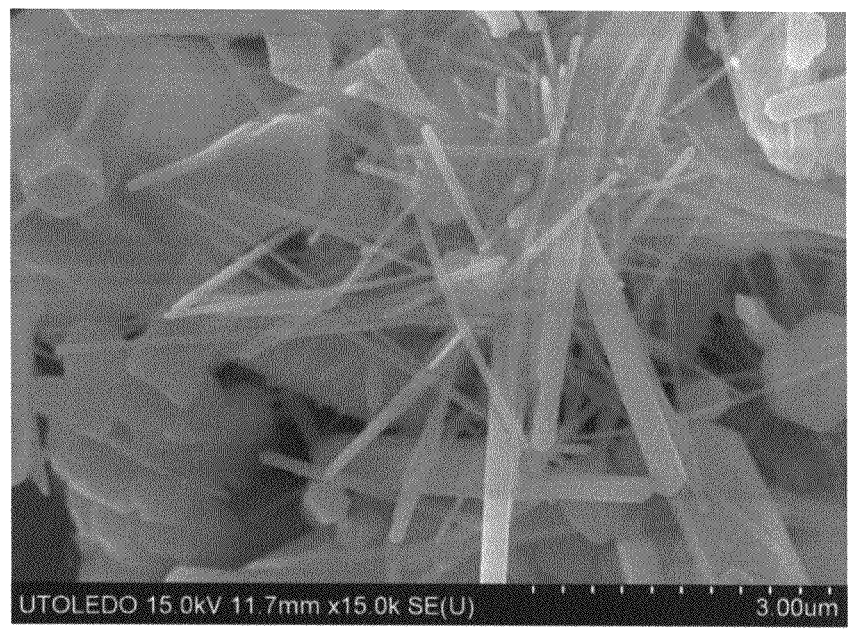
FIG. 22—SEM Micrograph of TCP-SC of very fine Nanowhiskers.

As can be seen in FIG. 21 and FIG. 22, reducing the cooling rate created ultrafine TCP nanoparticles with extremely high aspect ratios. While the vast majority of particles produced still had aspect ratios of approximately one, a reduction in the cooling rate and the subsequent increase in the crystal growth time period promoted the growth of much higher aspect ratio nanowhiskers.

In another embodiment, instead of using a slow cooling rate, quenching (i.e., fast cooling rate) can be used to alter nanoparticle formation.

By varying the growth kinetics of nanoparticle formation, particles of a controlled size and morphology with a known phase can be produced for a multitude of biomedical applications. High aspect ratio nanoparticles have several distinct advantages. Nanowhiskers, nanorods, nanotubes, etc. increased mechanical properties and high surface area to volume ratios. Improved mechanical properties are advantageous in applications where strength is needed, such as in bone tissue engineering scaffolds.

The nanowhisker particles are thus useful for gene and drug delivery applications. The increased surface areas allow additional signaling agents and therapeutic particles to be placed on the nanowhisker particle surface and/or higher drug concentrations can be delivered with lesser particulate matter. For example, signaling agents can be used to direct a particle to a specific tissue or cell type, which is directly correlated to the therapies efficacy and safety. Also, particles having the same cross sectional area as a spherical particle sharing the same diameter may be similarly ingested, but the increased length increases the particles' loading capacity.

Example 2

Calcium Phosphate Nanowhiskers for Gene Delivery

Use of High Aspect Ratio Calcium Phosphate Nanoparticles as Nonviral Carriers

The highly crystalline CaP nanowhiskers (i.e., high aspect ratio) of HA and TCN are useful for nonviral gene delivery. Calcium phosphates, in particular HA, are major constituents of bone and are bioactive both in vitro and in vivo. In addition, TCP is biodegradable.

The nanowhiskers were characterized using XRD, SEM, and TEM to confirm their compositions and morphology. Zeta potential measurements were also done to provide information on any potential charge interactions between a plasmid DNA or any other biological moiety and the particle surface.

Two distinct plasmids were used to study the ability of the nanowhisker particles to transfect mammalian cells. A commercial grade plasmid encoding for GFP under the CMV promoter was used. Also, plasmid DNA encoding for a BMP2-GFP fusion protein under the CMV promoter was used to demonstrate potential use in the orthopedic field. BMP2 is known to induce bone formation so these complexes may be used to promote bone regeneration. The complexes were used to transfect mouse bone marrow stromal cells (7F2, ATCC). GFP was visualized for both transfections using fluorescence microscopy.

The nanowhisker particles are useful in gene therapy to safely and efficiently deliver therapeutic nucleotide sequences to targeted cells. The nanowhisker particles provide advantages over viral methods which have a risk of insertional mutagenesis after viral integration. In addition, the immune response to viral proteins is a significant drawback for viral methods. The nanowhisker particles also provide advantages over nonviral methods which, while regarded as less efficient, are safer with respect to their lowered immune response.

The nanowhisker particles are also useful in conjunction with tissue engineering scaffolds, thus creating smart scaffolds that can more closely regulate tissue regeneration.

Attachment Efficiency to Calcium—Phosphate Nanowhisker Particles (CaPnw)

As can be seen in Table 4, DNA attachment efficiency generally increases with increasing w/w ratio. This is due to the fact that an increase in the number of particles is directly related to the total available surface area for DNA attachment. The more surface area that is available to the particles, the more likely it is that there will be successful DNA attachment. As such, in certain embodiments, particles can be mixed at around 100 w/w ratios of particles to DNA to maximize transfection efficiency. Table 4 shows the DNA attachment efficiency at varying w/w ratios of particles to DNA.

TABLE 4

DNA Attachment % Efficiency at Varying w/w Ratios of Particles to DNA

| w/w Ratio | HA | TCP | NaCl |
| --- | --- | --- | --- |
| 10 | 81.49 | 84.02 | 83.15 |
| 20 | 85.54 | 89.48 | 88.61 |
| 30 | 87.34 | 92.00 | 90.84 |
| 50 | 86.16 | 92.84 | 91.46 |
| 80 | 77.25 | 92.26 | 94.54 |
| 100 | 86.65 | 94.26 | 95.20 |

Characterize the Particles Via Zeta Potential Measurements

Figure 23:
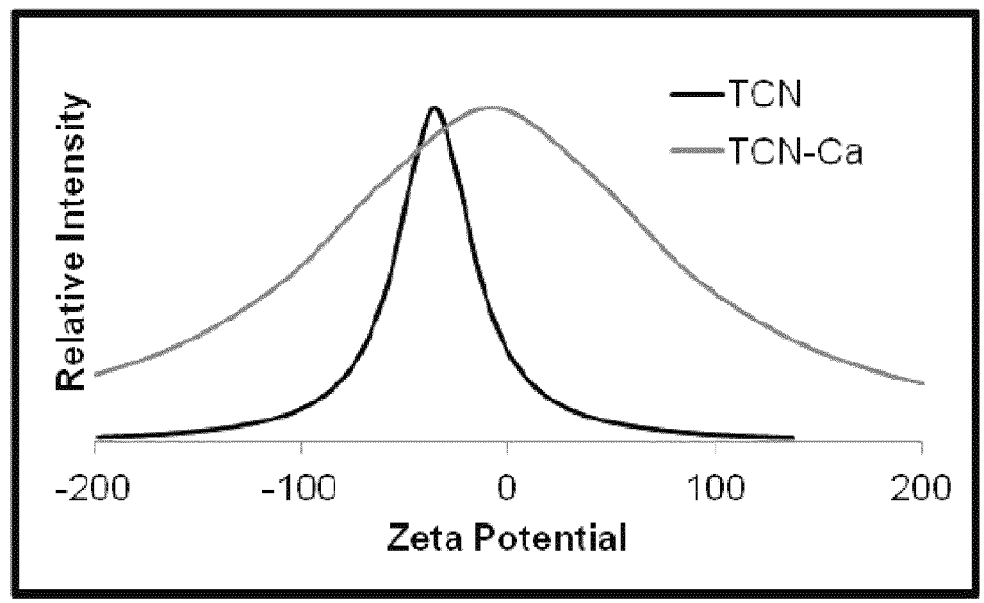
FIG. 23—Zeta Potential Shift after the Addition of CaCl2.

The zeta potential of the HA particles was measured to be the lowest, at around −10 mV, whereas the TCN was measured to be around −32 mV. DNA is well known to be negatively charged, therefore, it will not strongly attach via electrostatic interactions to a strongly negative particle. This is confirmed by the fact that that TCN variant had the lowest initial attachment efficiency. However, the addition of calcium ions to solutions containing strongly negative particles causes a surface deposition of calcium ions on those particles and therefore a change in the surface charge towards the positive direction. This can be seen in FIG. 23.

The addition of calcium chloride onto the TCN variant (indicated as TCN-Ca on the graph) causes both a shift in the positive direction and a peak broadening. This indicates that while the calcium deposited on the nanoparticles' surface, the calcium content in the solution was not sufficient to completely reverse the polarity of all surfaces. Nonetheless, this provides the necessary mechanism for anionic DNA attachment to the negative surface of the particles.

Figure 24:
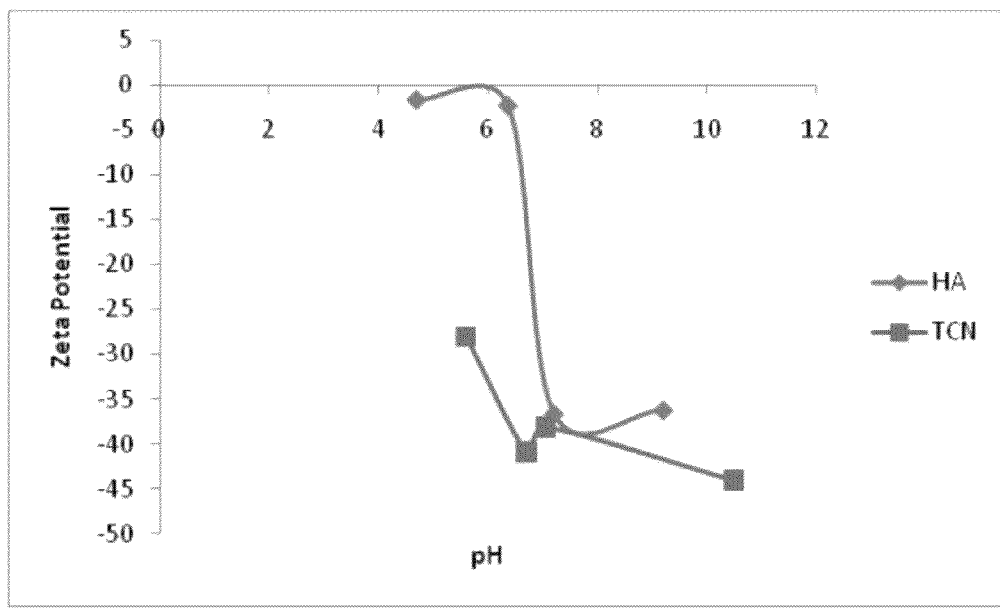
FIG. 24—Zeta Potential Measurements for HA and TCN at varying pH.

The IEP of the HA variant was found to be approximately 4.6. The zeta potential of TCN could not be determined below a pH of 5.6 as there was consistently an error message. It is thought that the particles begin to rapidly degrade below this pH and therefore no surface charge measurements could be made. (See FIG. 24).

Stability of Calcium-Phosphate Nanowhisker Particles

Figure 25:
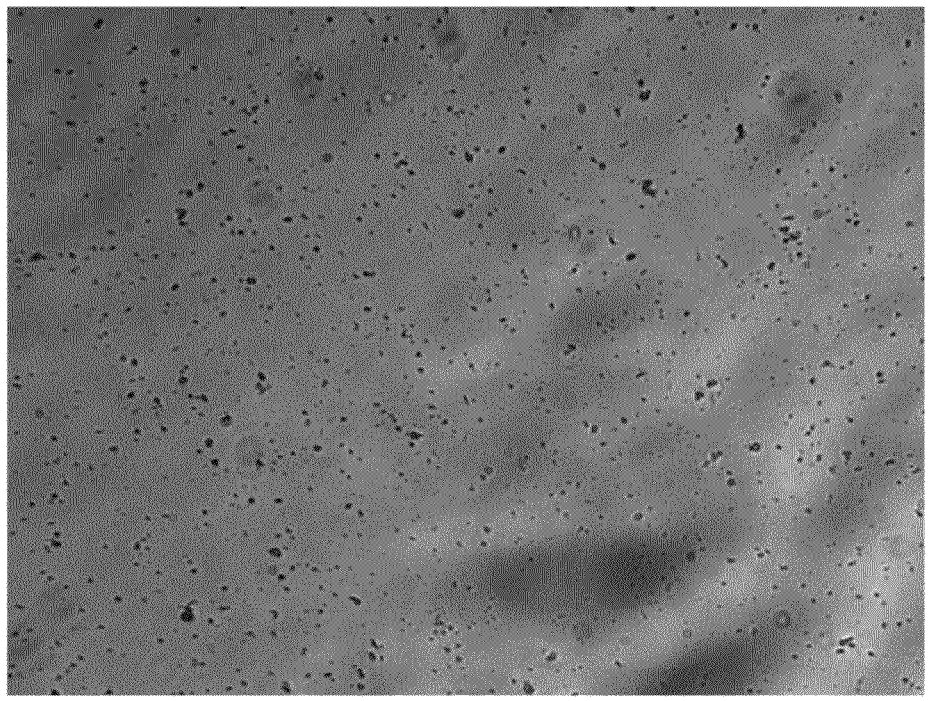
FIG. 25—Bright field image (100×) showing non-agglomerated HA nanowhiskers after 24 hours in culture.
Figure 26:
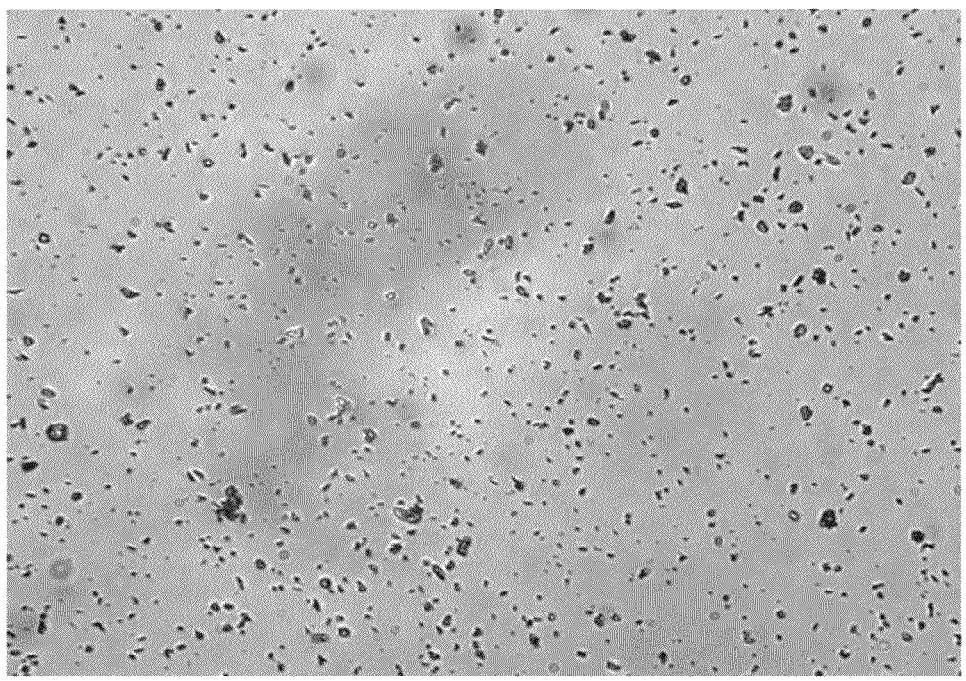
FIG. 26—Bright field image (100×) showing non-agglomerated optimized TCN nanowhiskers after 24 hours in culture.
Figure 27:
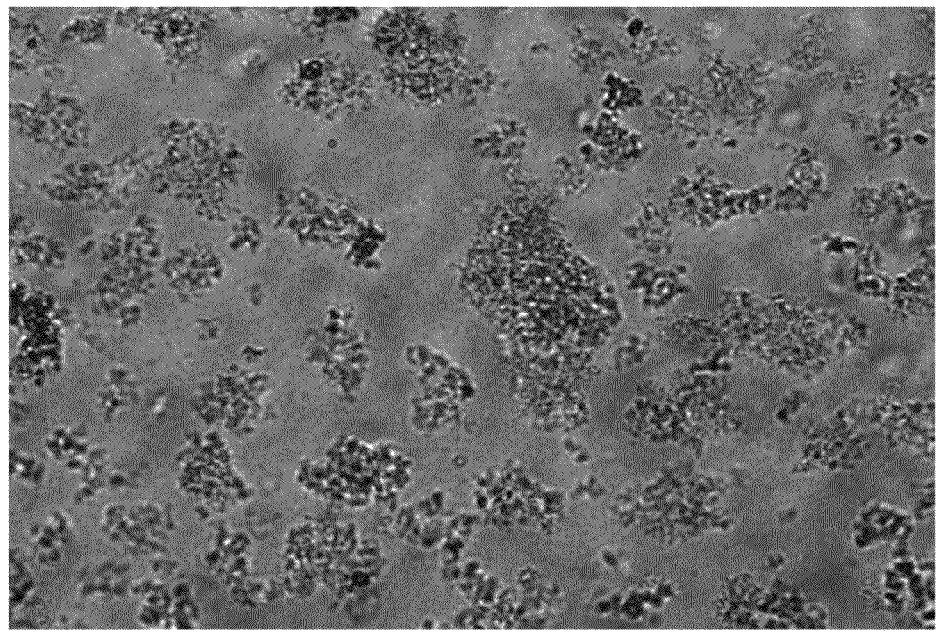
FIG. 27—Bright field image (100×) showing traditional calcium phosphate agglomeration after 24 hours in culture.

A zeta potential in excess of an absolute value of 30mv is regarded as a stable surface charge; thus, the particles will not further agglomerate in solution. As can be seen in FIG. 25 and FIG. 26, the Calcium-phosphate nanowhisker particles exhibit excellent stability and remain stable after 24 hours in complete media. In comparison, FIG. 27 shows the traditional CaP particulates 24 hours after transfection. These show that the traditional CaP particles have undergone significant agglomeration and are too large to be endocytosed. The enhanced stability of the Calcium-phosphate nanowhisker particles demonstrates that their therapeutic time window would be significantly longer than the traditional CaP particles.

Nanotoxicity

While calcium phosphates are regarded as biocompatible, the importance of examining nanoscale toxicity responses has become crucial in examining biological responses. The effect that unreacted ions resulting from material processing can have on the cellular environment is also an important consideration.

Figure 28:
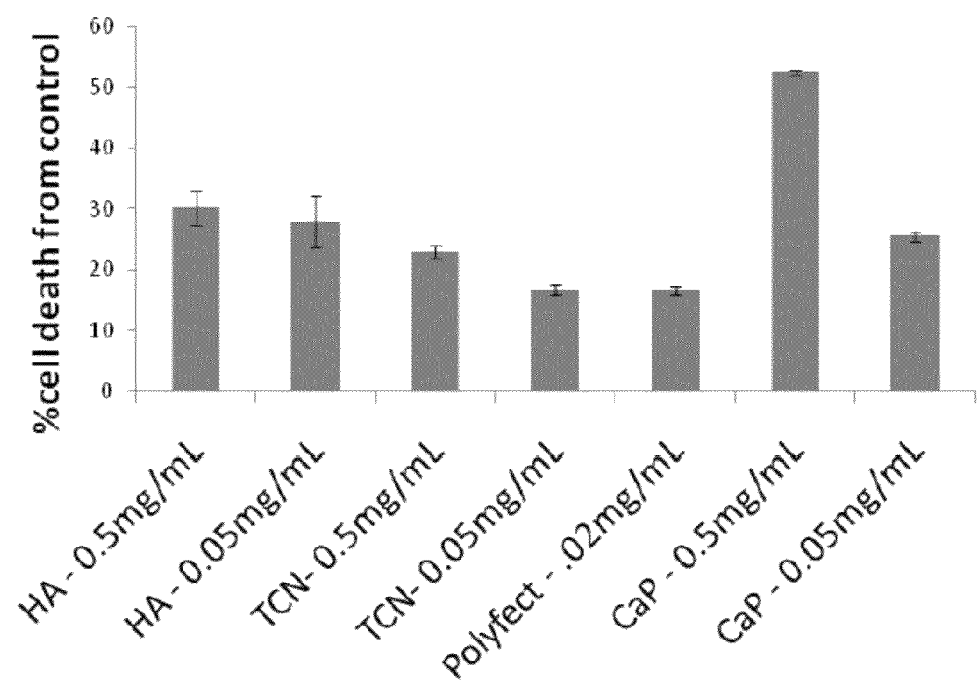
FIG. 28—Nanotoxicity effects of different transfection protocols on murine, bone marrow stromal cells (7F2, ATCC) after 24 hours (standard error bars).
Figure 29:
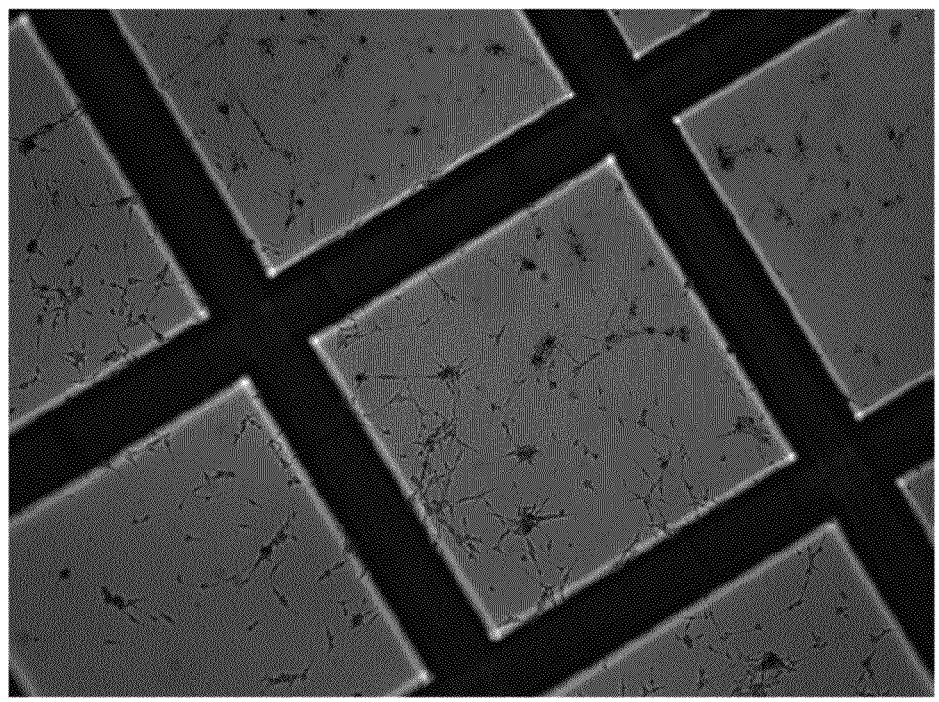
FIG. 29—Bright Field Image of TCP-gWIZ Transfected 7F2 (100×).
Figure 30:
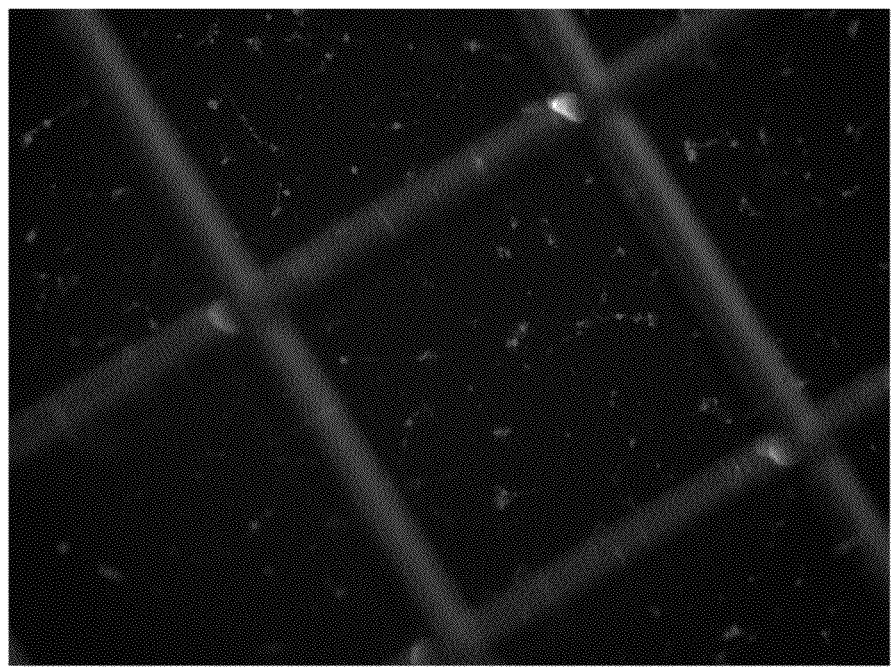
FIG. 30—Fluorescence Microscopy Image of TCP-gWIZ Transfected 7F2 (100×).

As can be seen in FIG. 28, the traditional CaP transfection method at a solution concentration of 0.5 mg/mL caused over 50% cell death as compared to cells alone (control). The calcium-phosphate nanowhisker particle transfections resulted in a substantially higher survival rate with toxicity rates of 30% for HA and 25% for TCN. While Polyfect showed a relatively low toxicity profile, it is believed to be due to its considerably lower recommended dosage amount. Polyfect was used according to the manufacturer's recommendations and was used at a considerably lower concentration than that used for either CaP transfection. Comparable toxicities can be seen between Polyfect at 0.02 mg/mL and 0.05 mg/mL TCN. This demonstrates that more than two times the concentration by weight of TCN can be used than Polyfect for therapeutic purposes with low cytotoxicity. The high toxicity observed with the traditional CaP is believed due to the unreacted ions used in the precipitation method. The method uses a calcium nitrate solution and an ammonium phosphate solution as the precursor salts for calcium and phosphate. No step exists to remove the residual ions after co-precipitation with the plasmid DNA, therefore the remaining species can have a toxic effect, as demonstrated here.

In the calcium-phosphate nanowhisker particles method, all residual ions are removed when the powders are washed with DI water. Therefore, the only toxic effects would be from the particles themselves or any degradation products. This is an additional and significant benefit of using the pre-manufactured calcium-phosphate nanowhisker particles which can be both sterilized and purified prior to their use.

Transfection Results

The ability of the calcium-phosphate nanowhisker particles to transfect two different cell lines with two different plasmids was tested. A 1:100 w/w ratio for DNA to calcium-phosphate nanowhisker particles for complexation was used in all of the transfection studies. The 7F2 cell line was used to test the ability of these particles to transfect an osteoblast like cell line, which is known to be difficult to transfect. gWIZ was used as a proof of concept plasmid, while the pBMP2-tGFP was used to show the possibility of using this delivery system to deliver a therapeutic protein. BMP-2 is an FDA approved protein therapy and is being widely investigated for use as a target for gene delivery.

The tGFP allows the production of the BMP-2 to be monitored using fluorescence microscopy. As can be seen by examining FIG. 29 to FIG. 33, the calcium-phosphate nanowhisker particles-gWIZ complexes achieve far superior transfection than the gWIZ alone to 7F2 cells. The gWIZ plasmid is under control of the CMV promoter which is not able to localize to the nuclear membrane. Calcium regulates the permeability of the nuclear pores; therefore, this may be one of the reasons that there is such a significant increase in transfection efficiency with the calcium-phosphate nanowhisker particles as compared to naked plasmid where no transfection was observed. Additionally, the anionic DNA may have difficulty in traversing the cellular membrane to even initiate the transport of the plasmid into the cell. The calcium-phosphate nanowhisker particles may be able to utilize some sort of receptor-mediated endocytosis or calcium regulated transport to increase cellular uptake of the plasmid DNA complexes.

Figure 31:
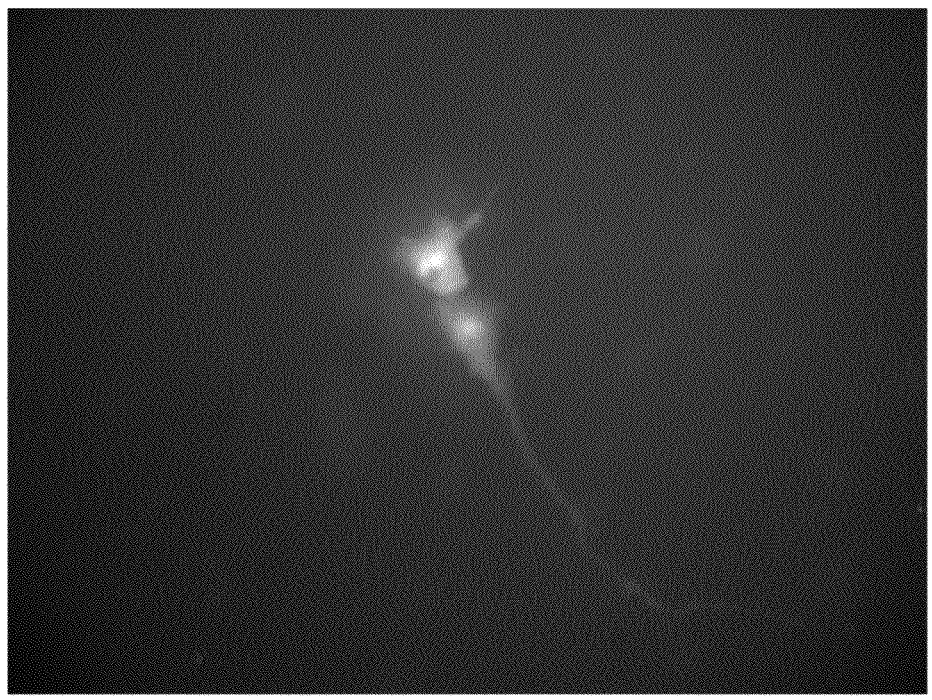
FIG. 31—Fluorescence Microscopy Image of HA-gWIZ transfected 7F2 cells at 48 hours (200×).
Figure 32:
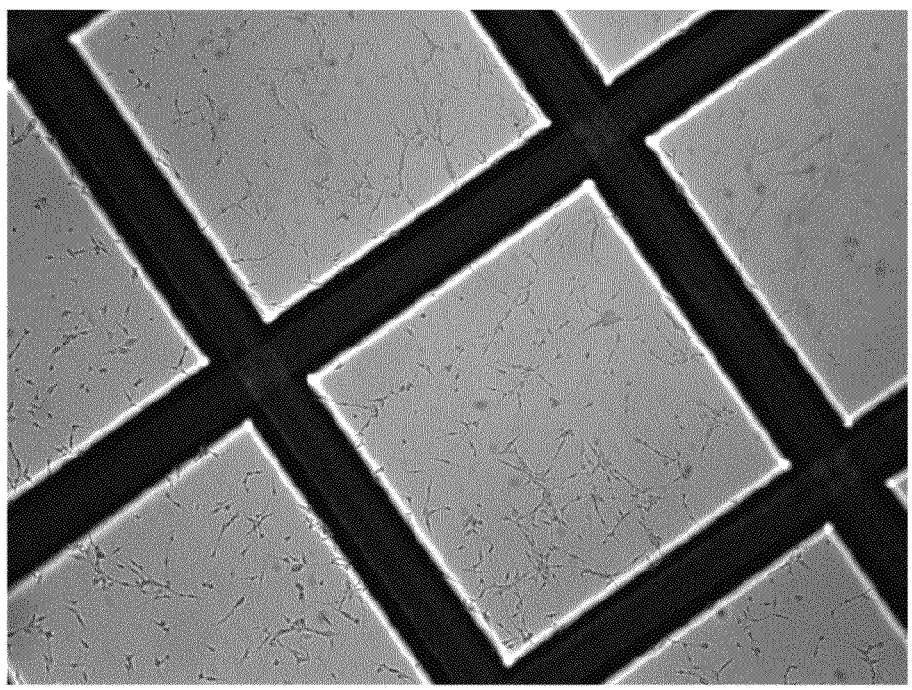
FIG. 32—Bright Field Image of Mouse Osteoblasts Transfected with naked gWIZ plasmid (100×).
Figure 33:
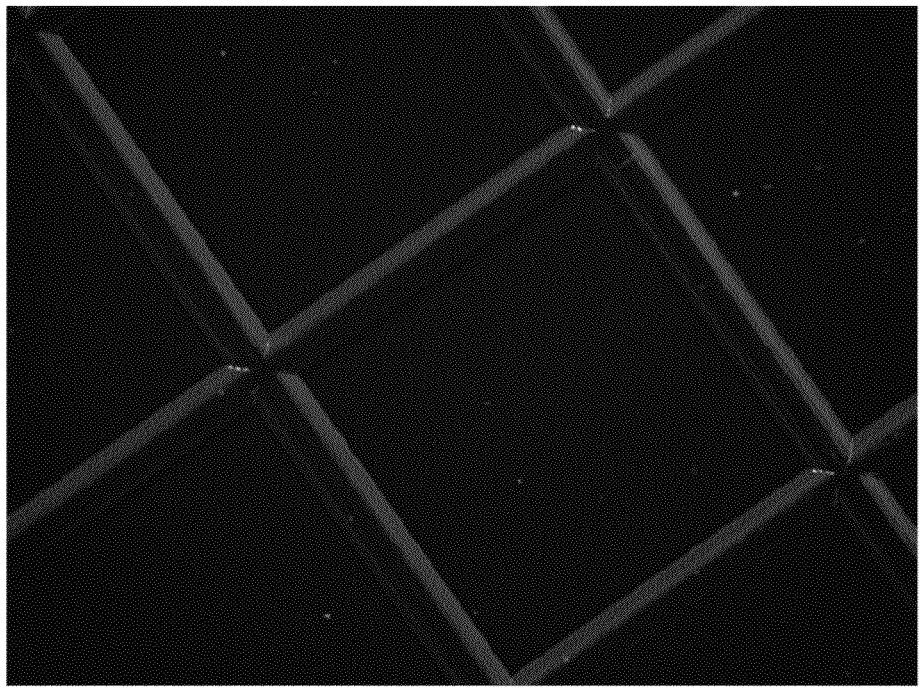
FIG. 33—Fluorescence Microscopy Image of Mouse Osteoblasts Transfected with naked gWIZ (100×).

FIG. 31 demonstrates that the HA variant was successful in passing the newly acquired GFP expressing gene onto its daughter cell after 48 hours in the 7F2 cell line. In order to test the efficacy of the particles to transfect other cell lines, HEK-293T cells were also used. The use of the gWIZ and pBMP2-GFP showed comparable efficiencies.

Figure 34:
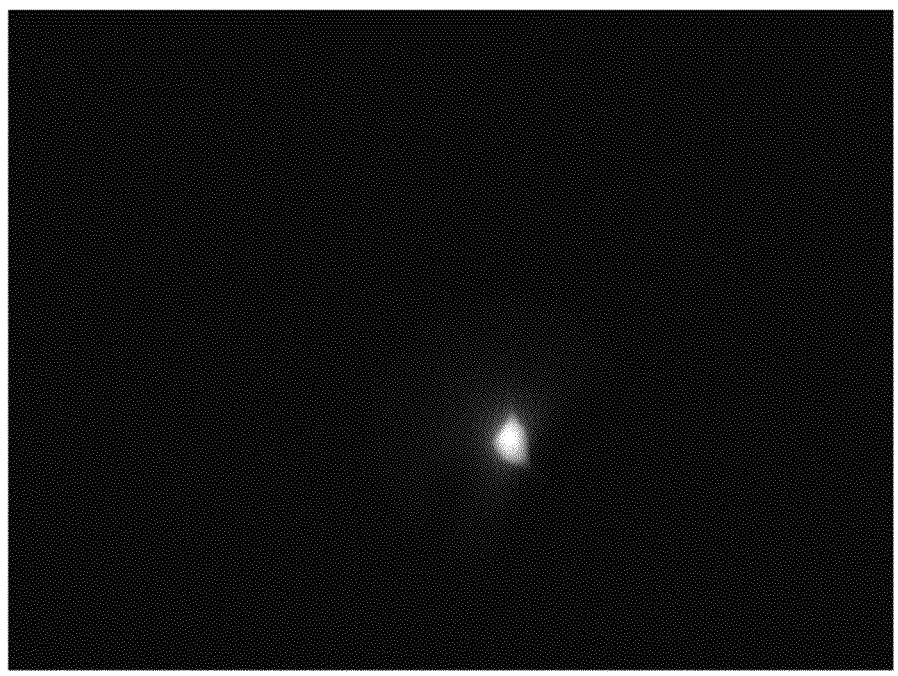
FIG. 34—Fluorescence Microscopy Image of a transfected HEK-293T Cell with pBMP2-GFP complexed to HA at 24 hours (200×).
Figure 35:
FIG. 35—Fluorescence Microscopy Image of a transfected HEK-293T Cell with pBMP2-GFP complexed to TCP at 48 hours (200×).

FIG. 34 and FIG. 35 show the capability of the HA and TCN variant to carry pBMP2-tGFP into the HEK-293T cells after 24 and 48 hours, respectively. This demonstrates the ability of this delivery system to be used to carry larger plasmids as the pBMP2-tGFP is approximately 2000 bp longer than the gWIZ plasmid, and additionally it shows the ability of the system to transfect more than one type of cell line.

The calcium-phosphate nanowhisker particles are capable of transfecting two separate cell lines using two different plasmids. The calcium-phosphate nanowhisker particles have a number of advantages over traditional CaP particles and the variety of organic nanoparticles currently used.

The calcium-phosphate nanowhisker particles systems have a high aspect ratio calcium phosphate particle useful for transfection. In addition, the TCN phase is now shown to be useful for any particle morphology.

Non-limiting examples of benefits of calcium-phosphate nanowhisker particles system over the traditional CaP system include, for example, solution stability, increased loading capacity per particle, and availability of other CaP phases. In addition, the calcium-phosphate nanowhisker particles may also be used in conjunction with tissue engineering scaffolds and will not further agglomerate in vitro or in vivo, unlike the current CaP particles.

The improved crystallinity of the calcium-phosphate nanowhisker particles may also be beneficial for load bearing applications as improved crystallinity is associated with improved mechanical strength. In addition, such particles may be used in a multifunctional approach to tissue engineering applications.

Example 3

Europium Calcium Phosphate Nanowhiskers

The nanowhisker particles described herein are also useful as fluorescent probes for imaging agents in order to optically elucidate mechanisms that can otherwise not be intrinsically observed. The high aspect ratio, highly crystalline hydroxyapatite nanoparticles are capable of fluorescence.

Also described herein is the inclusion of additional particles, such as the inclusion of europium or other lanthanide series atoms, which are substituted into the crystal lattice of the hydroxyapatite nanowhiskers during their synthesis. These particles can be visualized with a variety of excitation wavelengths from the UV range all the way to the near infrared. These particles exhibit relatively narrow emission bands which allows for their use in multicolor imaging applications.

The nanowhisker particles are not susceptible to limitations such as photobleaching, yet the nanowhisker particles provide yield high fluorescence, possess narrow emission/excitation peaks, exhibit good biocompatibility, and have high structural and dispersion stability in vitro and in vivo. The microwave assisted combustion synthesis method is also useful to produce a doped, high aspect ratio, highly crystalline, calcium phosphate nanoparticle that can be used in a variety of applications. One non-limiting benefit of using this synthesis method is that high aspect ratio nanoparticles of varying CaP phase can be produced.

In addition, the presently described method drastically reduces synthesis times and energy consumption, particles of a controlled shape can be produced, and highly crystalline, non-agglomerated nanowhisker particles with fluorescent properties can be produced. The nanowhisker particles may be utilized in association with the other technologies to provide still other dimensions of functionality. While europium is shown in the example herein, it is to be understood that it is within the contemplated scope of the present invention that other lanthanide series elements can be used.

Figure 36:
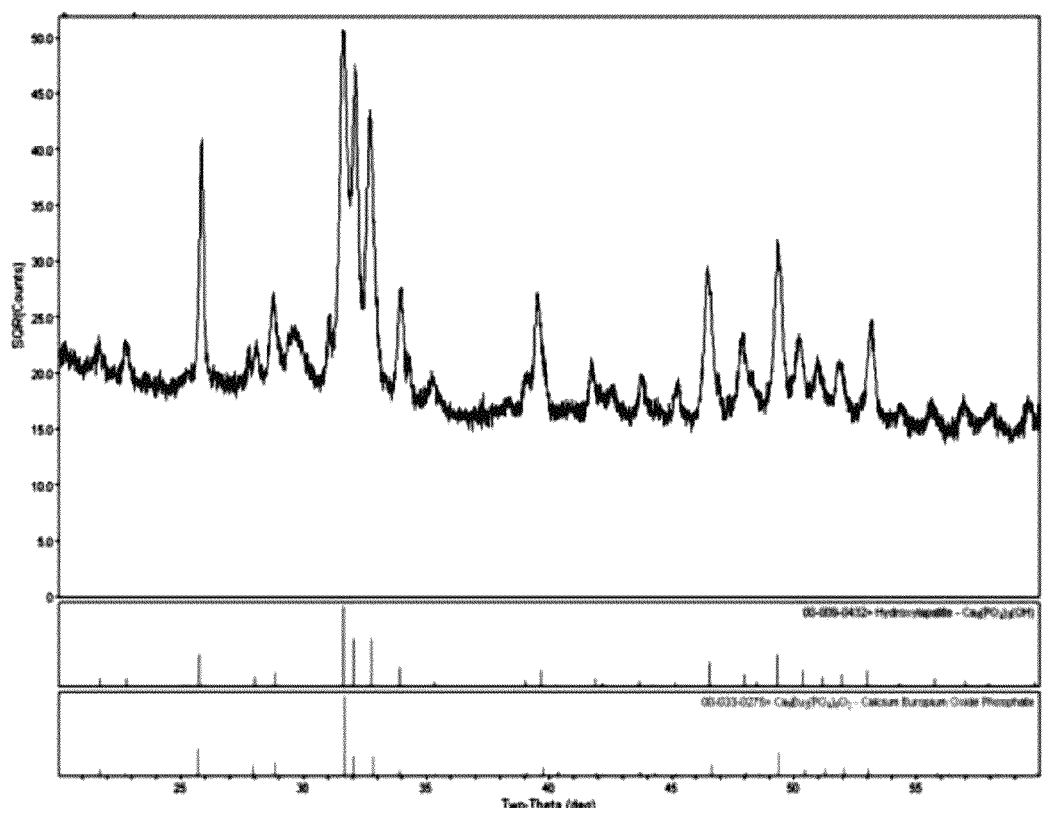
FIG. 36—XRD Spectrum of Europium Doped Hydroxyapatite Nanowhiskers.

FIG. 36 shows the XRD trace of the europium doped nanoparticles. The peaks correspond well with HA (JCPDS 00-009-0432) and a calcium phosphate whereby europium has substituted into a hydroxyapatite lattice for calcium (JCPDS 00-033-0275). This confirms that the addition of 5 mol % Eu did not change the predominant phase of the resultant calcium phosphate.

The results of 254, 285, and 300 nm excitation are shown in FIG. 36. An excitation wavelength of 254 nm yielded a $^5D_0 \rightarrow ^7F_1$ transition at 591 nm and a $^5D0 \rightarrow ^7F_2$ transition at 616 nm. The $^5D_0 \rightarrow ^7F_4$ transition was observed to occur at 696 nm with a 254 nm excitation. The emission peaks from 285 nm excitation further resolved a $^5D_0 \rightarrow ^7F_1$ transition at 575 nm emission and produced a second $^5D_0 \rightarrow ^7F_2$ at 631 nm emission. No new peaks were found using a 300 nm excitation. Table 5 compares the wavelengths determined in this work for five different transitions.

TABLE 5

| Fluorescence Transitions of Eu3+ in apatites | |
|---|---|
| Transition | λ emission (nm) |
| $^5D_0 \rightarrow F_0$ | 575 |
| $^5D_0 \rightarrow F_1$ | 591 |
| $^5D_0 \rightarrow F_2$ | 616, 631 |
| $^5D_0 \rightarrow F_3$ | 661 |
| $^5D_0 \rightarrow F_4$ | 696 |

Figure 41:
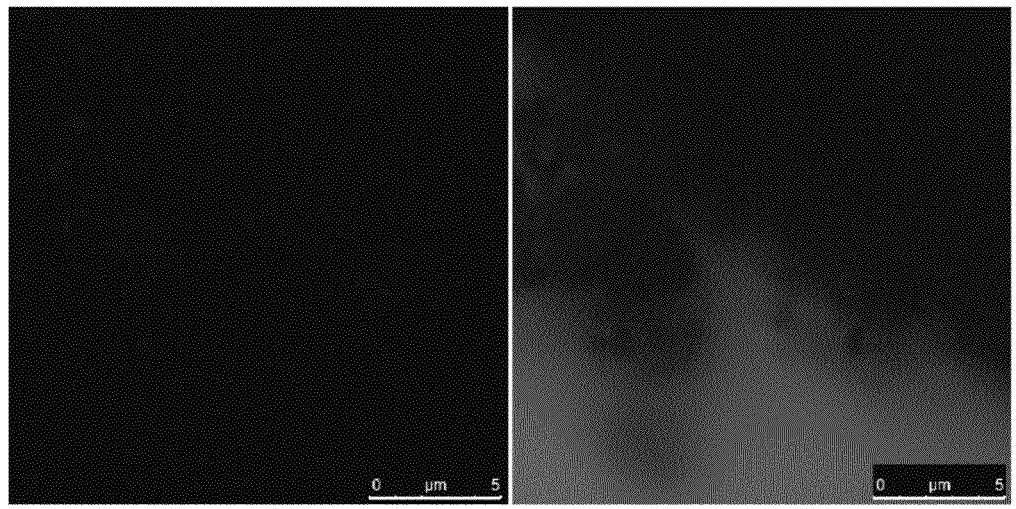
FIG. 41—Confocal Image at 514 nm excitation and 529-566 nm emission (left); corresponding confocal reflection (right).
Figure 42:
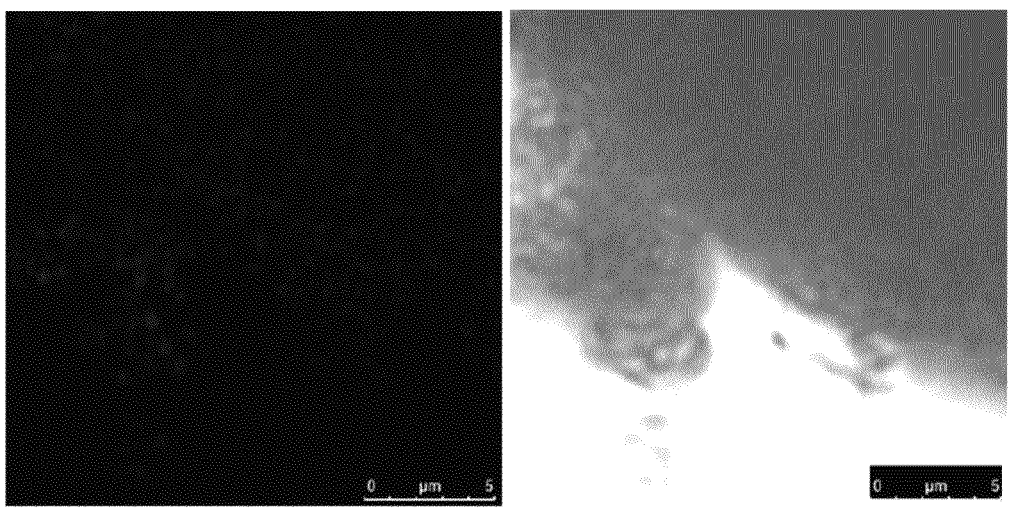
FIG. 42—Confocal image at 633 nm excitation and 639-662 nm emission (left); confocal reflection of corresponding image (right).
Figure 43:
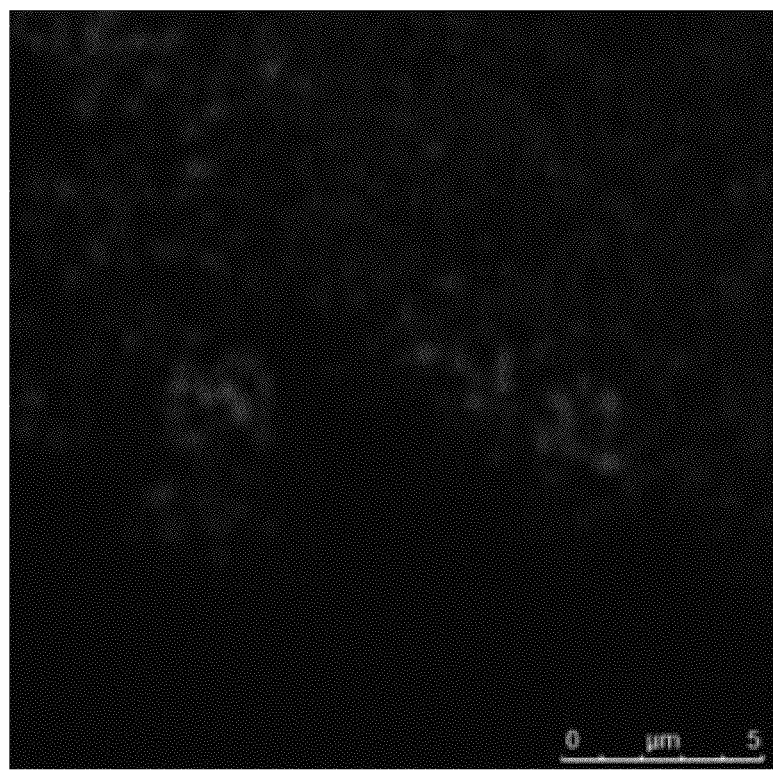
FIG. 43—Confocal Image at 633 nm excitation and 640-715 nm emission.
Figure 44:
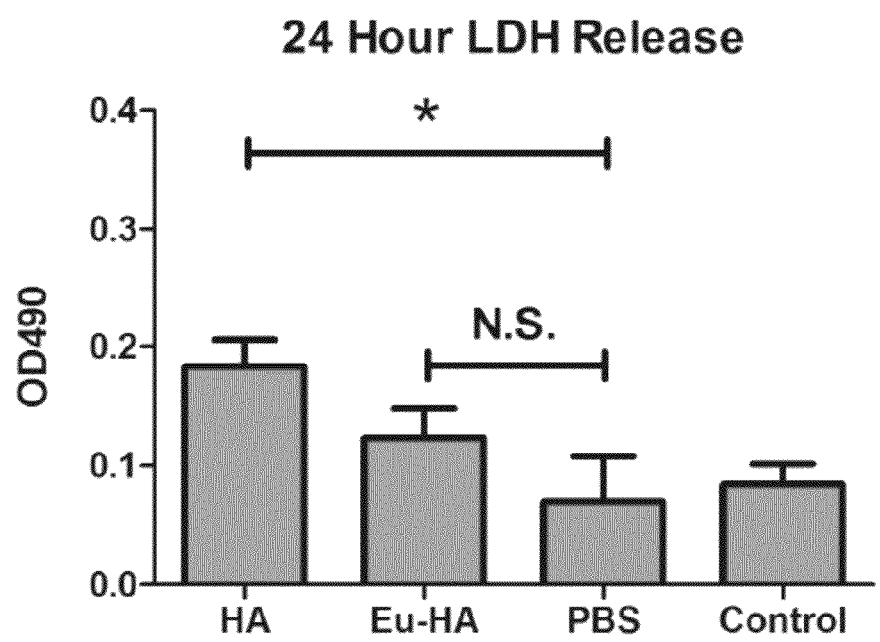
FIG. 44—Eu:HA nanoparticles do not exhibit significant cytotoxic effects after 24 hours. * indicates statistical significance at 95% confidence level with $p<0.05$ considered significant.

The particles were imaged in a confocal microscope to test their ability to be resolved as individual particles with a unique profile. Several different excitation wavelengths were tested to confirm an optimal fluorescence emission. Surprisingly, the particles were excited at 360 nm and 633 nm wavelength. The results of FIG. 41 through FIG. 43 show the ability of fluorescence to be generated with the 633 nm wavelength excitation source with optimal emissions being collected from 640 nm-715 nm. The emission wavelengths correspond well with the $^5D_0 \rightarrow ^7F_3$ and $^5D_0 \rightarrow ^7F_4$ transitions observed using UV excitation.

Confocal microscopes are able to use multiple, independent excitation wavelength parameters to simultaneously image multiple fluorescent probes which have been independently excited. The ability of these particles to fluoresce with a 633 nm excitation is beneficial for at least two reasons. First, the 633 nm wavelength is in the visible range. Many confocal microscopes are not fitted with a UV excitation capability. Therefore, the nanowhisker particles do not require any additional equipment to be used as fluorescent probes. As can be seen, the confocal images show that individual particles can be resolved. The nanowhisker particles are thus also useful as nanoprobes to investigate intracellular events such as endocytosis, phagocytosis, etc.

In vivo biophotonic imaging systems are capable of imaging live and larger samples than confocal microscopes. The 633 nm excitation is close to the near infrared range which thus allows for their use in in vivo imaging. In addition, in certain embodiments, since infrared wavelengths have greater penetration depth than those in the visible light range, the nanowhisker particles can be excited using near infrared wavelengths, and can be also used in the field of diagnostics. The fluorescence function of the nanowhisker particles allows the nanowhisker particles to be tracked throughout the entire living system and to monitor cellular events. Non-limiting examples of applications are bone remodeling, lung inhalation of high aspect ratio nanoparticles, intravenous particle injection, gene delivery, and liver accumulation.

Thus, the highly crystalline, high aspect ratio calcium phosphate nanowhisker particle has fluorescent properties that incorporate Eu3+ into the crystal lattice. The crystal structure of calcium phosphates provides lattice substitutions under the appropriate synthesis conditions. Some calcium ions are replaced in the crystal and therefore, the europium is able to substitute into the lattice. While the europium was not incorporated into every nanoparticle (as evident by the lack of fluorescence intensity at some locations), it is within the contemplated scope of the present invention that the mol % can be further optimized to maximize fluorescence.

Figure 37:
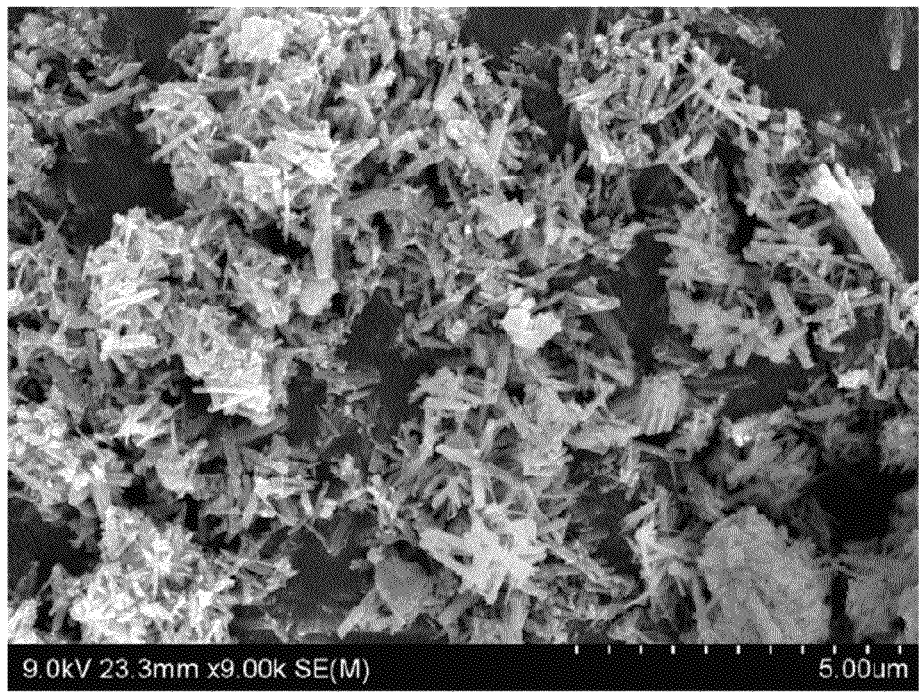
FIG. 37—SEM Micrograph showing the consistent production of high aspect ratio HA:Eu nanoparticles.
Figure 38:
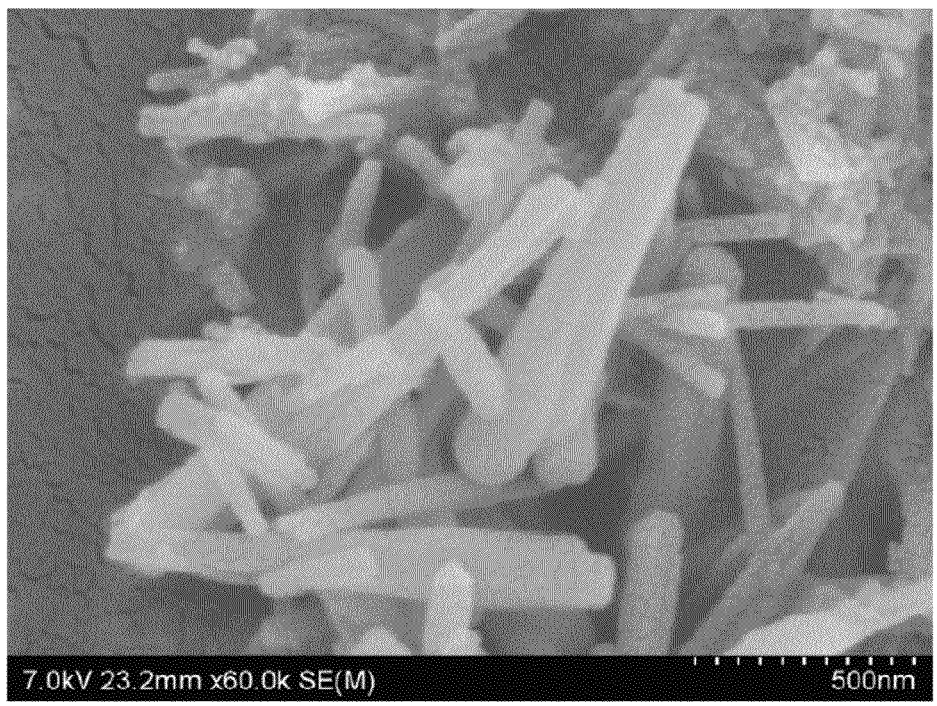
FIG. 38—SEM Micrograph showing high aspect ratio HA:Eu nanoparticles at high magnification.
Figure 39:
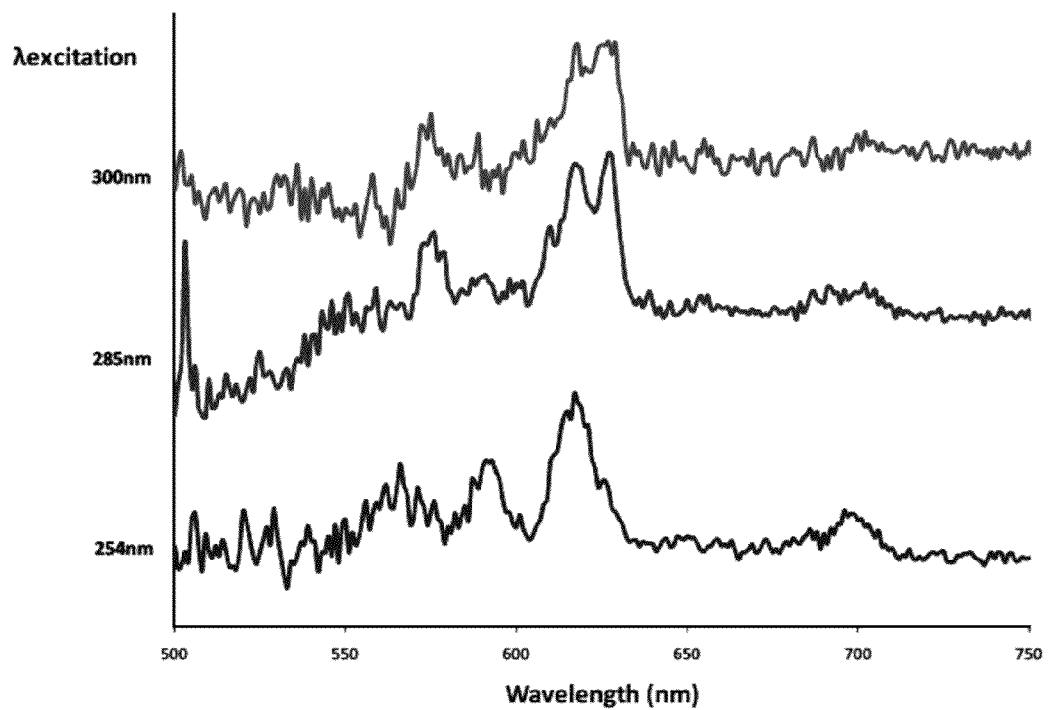
FIG. 39—Photoluminescence emission spectra for combustion synthesized HA:Eu.
Figure 40:
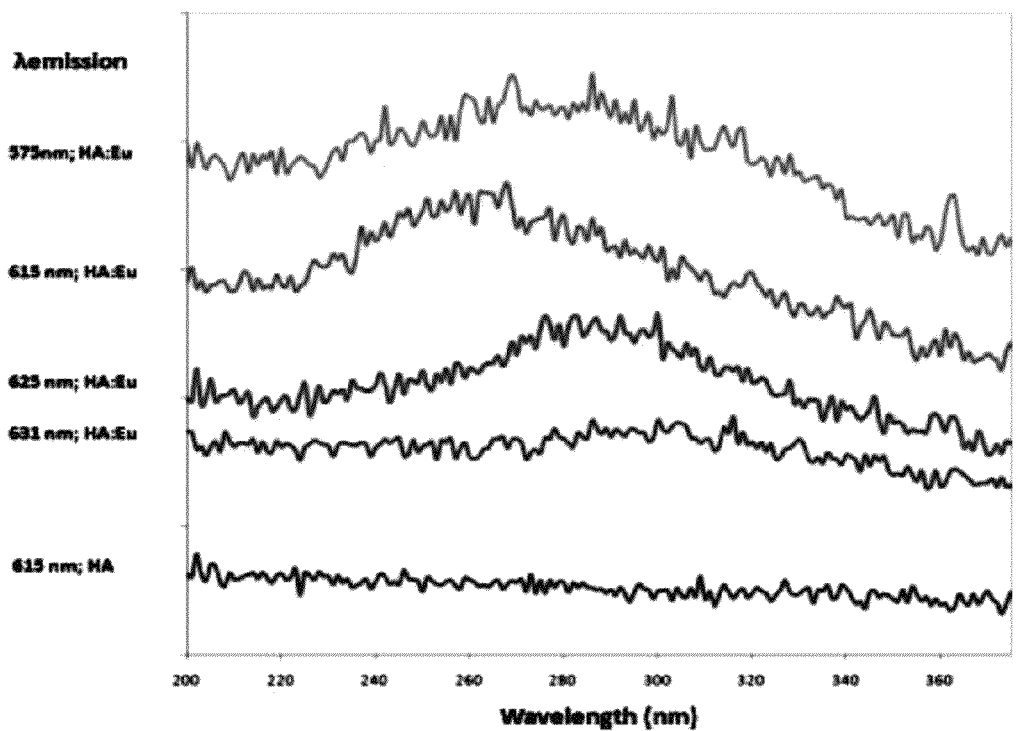
FIG. 40—Excitation Spectra for varying Emission Wavelengths.

The SEM micrographs in FIG. 37 and FIG. 38 demonstrate that the addition of europium nitrate to the synthesis method has not changed the general size scale or shape of the nanoparticles as compared to the synthesis of the HA Calcium-phosphate nanowhisker particles. FIG. 37 shows that particles with an aspect ratio greater than one are consistently achieved. The aspect ratio remains significantly greater than one with particle diameters remaining less than 100 nm as shown in FIG. 38. This demonstrates the flexibility of the synthesis method in that it can consistently produce high aspect ratio, highly crystalline nanoparticles with appropriate dopants.

100 μg of a 1 mg/mL Eu:HA or HA nanoparticles did not elicit significant LDH release (corresponding to a cytotoxic event) as compared to spontaneous release (control) of 7F2 cells. Therefore, the doped variants appear to be biocompatible from a cytoxicity perspective.

Example 4

Examples of Uses

A patient presenting a complex fracture in their ankle could normally require extensive grafting and perhaps orthopedic metal implants for proper healing. With this technology, they may now only require minimal grafting or a stem cell therapy with supplementation of the nanowhiskers containing the DNA promoting appropriate bone growth. This can represent a significant improvement in long term patient healing, reduce complications often seen with metal implants, and therefore an overall reduction in patient cost.

The storage life of these particles is much improved over other nonviral methods and therefore provides another advantage over the majority of the current particles.

Another advantage is that these particles have an increased loading capacity over traditional nanoparticles (due, at least in part, to their increased surface area) and therefore can be more individually tailored for the applications.

Their elongated shaped may also allow them to transgress the blood brain barrier, an elusive feat in the pharmaceutical industry.

A vaccine composition may be formed comprising at least one particle as described herein above, and a killed, attenuated, or live vaccine, or a decoy virus, or a particle coated with antigenic material. The vaccine composition may also include a pharmaceutically acceptable agent or other excipient including nucleic acids, nucleotides, oligonucleotides, peptides to transfect antigen presenting cells (APCs) or non-APCs via the process of cross-presentation. The vaccine composition may comprise a DNA vaccine, a CaP nanowhisker particle as described above, and a pharmaceutically acceptable carrier or adjuvant.

These vaccine compositions may be administered intradermally or intramuscularly. When administered intradermally, the vaccine compositions may be administered using a tattoo device.

A tattoo ink administered with the tattoo device may comprise CaP nanowhisker particles as described above. If desired, the tattoo ink administered with the tattoo device may comprise CaP nanowhisker particles as described above and may further include fluorescent material.

A phosphor-based light emitting diode (LED) may be formed comprising at least one particle as described herein above, and a coating material and an existing one or more color LEDs whereby the existing one or more color LEDs serve as the excitation source and the nanowhiskers or a doped nanowhisker is used with a coating material to change the light emission of the existing one or more LEDs.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

The publication and other material used herein to illuminate the invention or provide additional details respecting the practice of the invention, are incorporated be reference herein, and for convenience are provided in the following bibliography.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

What is claimed is:

1. A process for forming a calcium phosphate nanowhisker particle, comprising:
   i) exposing a mixture of a soluble calcium, a soluble phosphate, and urea to microwave energy for a predetermined period of time and at a predetermined energy level sufficient to cause an exothermic reaction; and thereafter,
   ii) cooling the mixture of step i) so that calcium phosphate nanowhiskers having a length:diameter aspect ratio of greater than about 1:1 are precipitated in a molten salt bath, wherein
   the mixture comprises an aqueous solution of $Ca(NO_3)_2$ and an aqueous solution of $KH_2PO_4$ at a ratio of about 1:0.38, by weight.

2. The process of claim 1, wherein the mixture further includes at least one additive comprised at least of NaCl; and, wherein the additive and soluble calcium are present at a ratio of about 3.5:1, by weight.

3. The process of claim 1, wherein the average aspect ratio of the particle is greater than about: 5:1; 10:1; 25:1 and/or 50:1.

4. The process of claim 1, wherein the mixture comprises $NaNO_3$, $Ca(NO_3)_2$, $KH_2PO_4$, $HNO_3$, and optionally one or more additives.

5. The process of claim 1, wherein the microwave energy is supplied at a frequency in a range of about 2.4 to about 2.5 GHz, and at a power in a range of about 550 W to about 650 W.

6. The process of claim 1, wherein the microwave energy is supplied at about 2.45 GHz and at power of about 600 W.

7. The process of claim 1, wherein the calcium phosphate nanowhisker particles formed comprise one or more of: hydroxyapatite particles, beta-tricalcium phosphate particles, and mixtures thereof.

8. The process of claim 1, wherein the mixture further includes at least one fluorescent material.

9. The process of claim 1, wherein the nanowhisker particle comprises a lanthanide rare earth doped Ca—P.

* * * * *